United States Patent

Morrison et al.

[11] Patent Number: 6,103,271
[45] Date of Patent: Aug. 15, 2000

[54] MICROENCAPSULATION AND ELECTROSTATIC PROCESSING METHOD

[75] Inventors: Dennis R. Morrison, Kemah; Benjamin Mosier, Houston, both of Tex.

[73] Assignee: The United States of America as represented by the Administrator of the National Aeronautics and Space Administration, Washington, D.C.

[21] Appl. No.: 09/079,770

[22] Filed: May 15, 1998

Related U.S. Application Data

[63] Continuation-in-part of application No. 08/349,169, Dec. 2, 1994, Pat. No. 5,827,531.

[51] Int. Cl.⁷ .................................................. A61K 9/50
[52] U.S. Cl. .................... 424/490; 424/450; 424/489; 424/491; 424/497; 424/498; 427/213.3; 428/402.21; 428/402.24; 514/772.3; 514/773; 264/4.32; 264/4.33
[58] Field of Search ........................... 424/489, 490, 424/450, 491, 497, 498; 427/213.3; 428/402.21, 402.24; 264/4.32, 4.33

[56] References Cited

U.S. PATENT DOCUMENTS

| | | |
|---|---|---|
| 4,201,691 | 5/1980 | Asher et al. ............................ 252/314 |
| 4,423,091 | 12/1983 | Iwasaki et al. ..................... 427/213.34 |
| 4,590,170 | 5/1986 | Akiyoshi et al. ....................... 281/529 |
| 4,619,795 | 10/1986 | Cohen ....................................... 264/4.6 |
| 4,921,706 | 5/1990 | Roberts et al. .......................... 424/450 |
| 4,936,901 | 6/1990 | Surgant, Sr. et al. ....................... 71/92 |
| 5,165,994 | 11/1992 | Kaler et al. .......................... 428/402.2 |
| 5,545,423 | 8/1996 | Soon-Shiong et al. ................. 424/484 |

*Primary Examiner*—James M. Spear
*Attorney, Agent, or Firm*—James M. Cate

[57] ABSTRACT

Methods are provided for forming spherical multilamellar microcapsules having alternating hydrophilic and hydrophobic liquid layers, surrounded by flexible, semi-permeable hydrophobic or hydrophilic outer membranes which can be tailored specifically to control the diffusion rate. The methods of the invention rely on low shear mixing and liquid-liquid diffusion process and are particularly well suited for forming microcapsules containing both hydrophilic and hydrophobic drugs. These methods can be carried out in the absence of gravity and do not rely on density-driven phase separation, mechanical mixing or solvent evaporation phases. The methods include the process of forming, washing and filtering microcapsules. In addition, the methods contemplate coating microcapsules with ancillary coatings using an electrostatic field and free fluid electrophoresis of the microcapsules. The microcapsules produced by such methods are particularly useful in the delivery of pharmaceutical compositions.

52 Claims, 5 Drawing Sheets

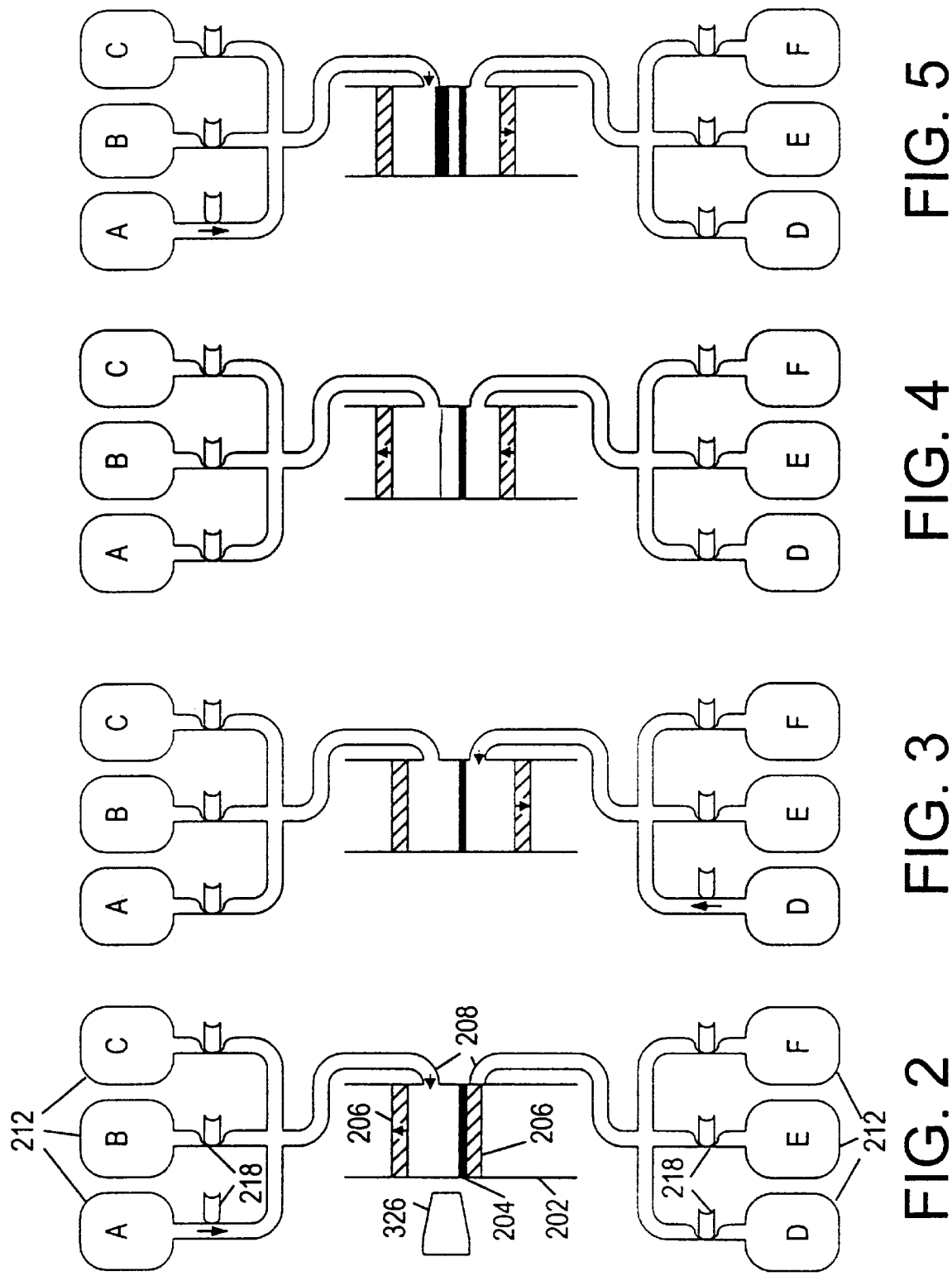

MICROENCAPSULATION AND ELECTROSTATIC PROCESSING METHOD

CROSS-REFERENCE TO RELATED APPLICATIONS

This application is a continuation-in-part of U.S. patent application Ser. No. 08/349,169 filed Dec. 2, 1994 (now U.S. Pat. No. 5,827,531), which is hereby incorporated by reference as though completely set forth herein. This application is further related to the following U.S. Patent Applications which are filed contemporaneously herewith:

(1) Application No. 09/079,741 entitled "In Situ Activation of Microcapsules" invented by Dennis R. Morrison and Benjamin Mosier, NASA Case No. MSC-22866-1;

(2) Application No. 09/079,833 entitled "Microencapsulation and belectrostatic Processing Device" invented by Dennis R. Morrison, Benjamin Mosier and John M. Cassanto, NASA Case No. MSC-22937-1-SB;

(3) Application No. 09/079,758 entitled "Externally Triggered Microcapsules" invented by Dennis R. Morrison and Benjamin Mosier, NASA Case No. MSC-22939-1-SB;

(4) Application No. 09/079,766 entitled "Microencapsulated Bioactive Agents and Method of Making" invented by Dennis R. Morrison and Benjamin Mosier, NASA Case No. MSC-22936-1-SB.

Each of these applications is hereby incorporated by reference as though completely set forth herein.

GOVERNMENT LICENSE RIGHTS

The invention described herein was made by employees of the United States Government and may be manufactured and used by or for the Government of the United States of America for governmental purposes without the payment of any royalties thereon or therefor.

BACKGROUND OF THE INVENTION

A. Field of the Invention

The present methods are directed to the formation of multi-layered, microcapsules containing a variety of compounds, including pharmaceuticals. The present methods rely on controlling fluid shear forces in the microcapsule forming solutions. This low-shear approach to microcapsule formation yields more spherical microcapsules and a desirable size distribution. Methods are also provided for coating microcapsules with polymeric coatings. One such method involves the use of electrostatic fields to facilitate coating microcapsules with polyvinyl pyrrolidone.

B. Description of the Related Art

Many drug and enzyme therapeutics cannot be injected intravenously. Others can be injected, but rapidly degrade before reaching the target tissue. Some drugs and enzymes are cleared from the blood by the liver or kidneys so quickly that their biological half-life is too short to be of therapeutic value. Still other drugs are insoluble in aqueous solutions. Since intravenous injection in hydrocarbon solvents is not well tolerated by patients, such drugs are difficult to administer.

One method for overcoming these limitations is encapsulation into microcapsules or liposomes. Encapsulation of therapeutics can enable delivery to target organs where they can be released. Incorporation of therapeutics into microcapsules facilitates delivery by parenteral injection, nasal inhalation and dermal administration and provides for sustained drug release.

The size and shape of the microcapsules is critical for the distribution and drug delivery in the tissues. Typically, microcapsules of 1–20 micron diameter are ideal for intravenous administration, whereas, 50–300 micron diameter microcapsules are used for intraarterial delivery and 300 micron or greater for intraperitoneal administration. In each size range, highly uniform microspheres are needed for maximum packing densities and maximum drug payload delivery to target organs or tumors.

Microcapsules, such as liposomes, can be formed from amphiphilic molecules, such as phospholipids, that are capable of assembling into bilayers when dispersed in aqueous solutions at concentrations at or above their critical micelle concentrations. Typically, in liposomes that carry pharmaceuticals, the pharmaceutical is dissolved in the aqueous phase. However, drugs of limited solubility in aqueous solvents are difficult to incorporate into liposomes. Lipophilic drugs in liposomal formulations are only carried, if at all, in the hydrophobic region of the lipid bilayer. Some drugs are so insoluble that they do not associate with the bilayer and, therefore, have very low encapsulation efficiencies. Certain liposomal drug formulations, including anti-tumor liposomes containing doxorubicin [Gabizion et al. 1992] or muramyl tripeptide have been studied extensively in clinical trials.

Other methods of forming microcapsules are based on liquid-liquid dispersions of aqueous drugs and organic solvents. The dispersion methods often require emulsification of the aqueous phase into organic carrier solutions by shear, bubbling or sonication. These methods typically produce water-in-oil (WIO) type liposomes, for which a second requisite step is the removal of the organic solvent (typically by evaporation) to form reverse-phase evaporation vesicles or stable plurilamellar vesicles. These vesicles are rarely spherical and their size distribution is quite heterogeneous. Typically, in order to generate multilamellar vesicles, film casting with organic solvents, hydration and sizing using filtration through inert membrane filters is required [Talsma and Crommelin 1992]. Sophisticated, multi-step emulsion technology is required and yields of uniform type and size are often very low.

Liquid microemulsions also have been developed as drug delivery systems, especially for drugs that are poorly soluble in aqueous carriers. A microemulsion typically contains droplets in the range of 0.1 to 1 micron in diameter. Such microemulsions are characterized by very fluid and dynamic micelles which are formed by sequential mixing one immiscible phase with another using surfactants and co-surfactants [Bhargava et al. 1987]. Typically, surfactants that produce water-in-oil (W/O) microemulsions have a hydrophilic-lipophilic balance (HLB) rating of 3 to 6, while those that produce oil-in-water (O/W) microemulsions have an HLB of 8 to 18. The surfactants can be non-ionic, ionic, or amphoteric. Often, medium chain-length alcohols are added as the co-surfactant in the last step in achieving the final microemulsion.

The major disadvantages of microemulsions is that each micelle (liquid capsule) is too small (typically, less than 1.0 micron) for deposition in larger vascular beds when administered by intravascular injection. Therefore, microemulsions are not suitable for chemoembolization type treatment of vascularized tumors.

Additionally, since microemulsions are true colloidal suspensions, they cannot be scaled up to large enough size for many intravascular drug delivery applications. Microemulsions formed with lipid soluble anti-tumor agents and low-density lipoproteins (LDLS) have been used to target drugs to neoplastic cells that require large amounts of cholesterol for synthesis of cell membranes [Halbert et al. 1984]. However, LDLs also attract phagocytes making the amount of drug actually delivered to the tumors and thence the therapeutic dose difficult to determine.

Solid matrix microspheres may be also used for transporting adsorbed drugs within the matrix. For instance, U.S. Pat. No. 4,492,720 to Mosier disclosed methods for making microspheres to deliver chemotherapeutic drugs (including Cis-Platinum) to vascularized tumors. This method of preparing microspheres is accomplished by liquid encapsulation and solid-phase entrapment wherein the water-soluble drug is dispersed in a solid matrix material. The method involves dissolving the aqueous drug and the matrix material in an organic solvent, in which they are mutually soluble, then dispersing this mixture in a second organic solvent to form an emulsion that is stable enough for intravascular injection.

Other solid-matrix approaches have utilized copolymers such as polyvinyl chloride/acrylonitrile dissolved initially in organic solvents to form microparticles containing aqueous enzyme solutions. U.S. Pat. No. 3,639,306 to Sternberg et al. discloses a method of making anisotropic polymer particles having a sponge-like inner support structure comprising large and small void spaces and an outer, microporous polymer film barrier. A multiple-step batch process is used which entails removal of the organic solvents used to dissolve the polymers prior to addition of aqueous components.

Solid-matrix microspheres, however, are often not perfect spheres thereby limiting the packing density. Additionally, many drugs cannot be trapped or adsorbed in these systems at effective concentrations and drug-release rates are often not constant.

Density-driven phase separation and stratification into horizontal layers of the immiscible solutions used to form microcapsules presents a major difficulty in the commercial preparation of microcapsules. This problem limits microcapsule yields and leads to the creation of irregularly shaped capsules of variable sizes. Non-uniformity in capsule preparations limits microcapsule packing density thereby limiting the quantities of drug that can be delivered to target sites. Even when microcapsules are formed, these forces destabilize them in some cases causing them to burst.

These problems have been overcome to a limited extent through the use of multi-step, batch processes that include mechanical mixing and solvent evaporation steps [Talsma and Crommelin 1992]. However, each batch step suffers losses that reduce overall efficiencies.

Conventional methods do not permit simultaneous formation of the outer skin as the microcapsule itself is formed. Many conventional therapeutic microspheres have natural phospholipid outer skins (usually in combination with cholesterol and a fatty amine) and therefore are subject to elimination by immune cells. Other conventional methods use sialic acid and other coatings on the lipid bilayer to mask the liposomes from detection by the scavenging systems of the body. Without an adequate outer skin, microcapsules often coalesce thereby reducing shelf life.

For instance, U.S. Pat. No. 4,855,090 to Wallach, discloses a method of making a multilamellar lipid vesicle by blending an aqueous phase and a lipophilic phase using a high shear producing apparatus. The lipophilic phase is maintained at a high temperature (above the melting point of the lipid components) and is combined with an excess of the aqueous phase, which is also maintained at a high temperature. U.S. Pat. No. 5,032,457 to Wallach discloses a paucilamellar lipid vesicle and method of making paucilamellar lipid vesicles (PLV). The method comprises combining a nonaqueous lipophilic phase with an aqueous phase at high temperatures and high shear mixing conditions, wherein the PLVs are rapidly formed in a single step process.

U.S. Pat. No. 4,501,728 to Geho et al. discloses the encapsulation of one or more drugs or other substances within a liposome covered with a sialic acid residue for masking the surface of the membrane from scavenging cells of the body utilizing techniques known for the production of liposomes. In one embodiment, additional tissue specific constituents are added to the surface of the liposome, which cause attractions to specific tissues. Similarly, U.S. Pat. No. 5,013,556 to Woodle et al. provided methods for making liposomes with enhanced circulation times. Liposomes created by this method contain 1–20 mole % of an amphipathic lipid derivatized with a polyalkylether (such as phosphatidyl ethanolamine derivatized with polyethyleneglycol). U.S. Pat. No. 5,225,212 to Martin et al. discloses a liposome composition for extended release of a therapeutic compound into the bloodstream, the liposomes being composed of vesicle-forming lipids derivatized with a hydrophilic polymer, wherein the liposome composition is used for extending the period of release of a therapeutic compound such as a polypeptide, injected within the body. Formulations of "stealth" liposomes have been made with lipids that are less detectable by immune cells in an attempt to avoid phagocytosis [Allen et al. 1992]. Still other modifications of lipids (i.e., neutral glycolipids) may be affected in order to produce anti-viral formulations (U.S. Pat. No. 5,192,551 to Willoughby et al. 1993). However, new types of liposomes and microcapsules are needed to exploit the various unique applications of this type of drug delivery.

U.S. Pat. No. 4,201,691 to Asher et al. discloses a method for forming microcapsules from immiscible liquids wherein one fluid is forced under pressure through a porous membrane into a second fluid to form a dispersion of small bubble-like microdroplets. The pressure drop across the porous membrane determines the amount and size of the microdroplets or microcapsules in the resulting dispersion. The dispersion is forced through a porous fluid dispersing layer into the outlets of a nonporous material and exits the outlets as microcapsules. The microcapsule size distribution in these preparations is limited by the immutable physical characteristics of the porous fluid dispersing layer containing the multiphase dispersion just prior to its passage through the outlets. The Asher process is limited to the production of two layered microcapsules and it does not allow for coating or electrodeposition of additional coatings of microcapsules prior to transfer to another vessel.

Microencapsulation of liquid droplets has been accomplished by forcing aqueous solutions through a nozzle to create an aerosol within a cloud chamber containing an encapsulating material such as wax in vapor phase. Microcapsules are formed by passage of the liquid microdroplet through a coating vapor. In these systems the formation and curing of the outer capsule layer must occur before the microcapsules reach the walls of the cloud chamber. In a variation of this method, an electrostatic field is introduced into the cloud chamber. The field causes an electrostatic attraction between the coating material and surface of the oppositely charged liquid microdroplet. Yamati et al., Illinois. Inst. Of Technology Research Institute (IITRI) 1982; "Microencapsulation in Space (MIS)" on Shuttle Flight STS-53, Dec. 1992.

Microcapsules formed in cloud chambers are limited to diameters of less than 1 micron because of free fall dynamics that tend to break up larger microdroplets. Moreover, the formation time of microcapsules in cloud chambers is limited to the residence time of the droplet in its trajectory through the chamber. If the shell does not form before the droplet collides with the chamber wall, the microcapsule is destroyed. The fluids that can be used to form microdroplets also limit the technique. Only those fluids with suitable aerosol forming characteristics can be used and those fluids must be charged or they cannot be coated by the oppositely charged coating materials in the chamber. Furthermore, the process can only be used to create microcapsules having two layers and it does not allow for immediate coating or electrodeposition with additional charged coatings.

It is known that microgravity can be advantageously utilized to induce and maintain crystal growth due to the lack of density driven convective flow in liquids. U.S. Pat. No. 4,909,933 to Carter et al. discloses an apparatus for carrying out crystallization of proteins and chemical syntheses by liquid-liquid diffusion in microgravity environments. The apparatus comprises a housing having a plurality of chambers and a valve which separates at least two of the chambers so as to allow controlled fluid flow.

The disadvantages of conventional liposomes or microcapsules include manufacturing methods that require many batch process steps to: 1) form the liposomes, 2) remove unwanted organic solvents, detergents, and 3) harvest the proper size and shape microparticles for optimum pharmacologic efficacy [Talsma and Crommelin 1992]. Also conventional liposomes often use natural lipids and lecithins (from eggs, soybeans and other inexpensive sources) which attract phagocytic immune cells that rapidly remove the liposomes from the circulatory system before they arrive at the target tissue. This creates variable dose-responses making calculations of pharmacokinetics and therapeutic doses very difficult [Allen 1988]. Major difficulties with commercial preparation of microcapsules often involves density-driven phase separation of the immiscible carrier fluids, especially when forming water/oil systems.

These drawbacks limit the yield, make it difficult to harvest the proper size particle, result in microparticles that are not spherical nor uniform in size, thereby limiting the packing density (and drug payload delivered) when the microcapsules arrive at the arterioles or capillaries in the target issues. Liposomes have a bilayer outer membrane which requires that the entrapped drug must be soluble in both the aqueous and lipid phases in order to outwardly diffuse. This limits the type of drugs that can be released from conventional liposomes and the mole ratio of aqueous to lipid phases limits the amount of lipid drug that can be delivered.

New methods are needed for forming spherical multilamellar microcapsules having alternating hydrophilic and hydrophobic liquid layers, surrounded by flexible, semi-permeable hydrophobic or hydrophilic outer membranes which can be tailored specifically to control the diffusion rate. In particular, methods of making such microcapsules are needed which do not rely on batch processes involving, mechanical mixing and/or solvent evaporation. Moreover, there is clearly a need for methods and compositions that allow for uniform size and more spherical microcapsules. Methods are needed for controlling microcapsule formation such that microcapsules of defined diameters can be produced in a single apparatus independently of an immutable fluid dispersing layer. These methods should also be capable of producing microcapsules having a plurality of shells around their cores and therefore allow coating microcapsules with protective polymeric shells. New methods of coating microcapsules with polymeric shells are needed so that microcapsules having diameters greater than 1 micron can be coated. Microcapsules produced by such improved methods would be particularly useful in the delivery of pharmaceutical compositions.

SUMMARY OF THE INVENTION

Accordingly, methods are provided for forming spherical multilamellar microcapsules having alternating hydrophilic and hydrophobic liquid layers, surrounded by flexible, semi-permeable hydrophobic or hydrophilic outer layers which can be tailored specifically to control the diffusion rate. In particular, methods are provided for making microcapsules that do not rely on batch processes involving mechanical mixing and/or solvent evaporation. Methods and compositions provided herein allow for the production of more spherical microcapsules having a more uniform size. The methods can be used to control microcapsule formation such that multilamellar microcapsules of defined diameters a reproduced within a single apparatus without the need for an immutable fluid dispersing layer. Methods are also provided for coating microcapsules with protective polymeric shells. These methods can be used to coat microcapsules having diameters greater than 1 micron. Microcapsules produced by such improved methods are useful in the delivery of pharmaceutical compositions.

In one embodiment of the present invention, a device is provided which is suitable for carrying out the method of the present invention. The device comprises two chambers separated by a porous barrier. Typically, a first solution is introduced into one chamber through an inlet port, and a second solution is introduced into a second chamber through another inlet port. The two solutions are brought together at the porous barrier which stabilizes interface and suppresses mixing between the two solutions. After the solutions have been introduced and have become quiescent, the interface is gently separated from the filter. At this point, spontaneous formation of microcapsules at the interface occurs. In some cases, fluid motion may be provided to induce microcapsule formation. Where fluid motion is provided, the fluid shear between solutions is limited to less than 100 dynes/cm$^2$. This controlled low-shear approach to microcapsule formation yields spherical microcapsules having desirable size distributions.

Microcapsules formed by the present methods range in size from diameters of 1 micron to over 300 microns. The larger diameters are useful for intraarterial chemoembolization of tumors while smaller microcapsules can be used for intravenous administration of drugs. Microcapsules having diameters of over 300 microns are useful in formulations of pharmaceutical compounds for intraerperitoneal administration. Generally, smaller microcapsules are made when shearing forces are larger. The use of increasing amounts of fluid shear between solutions reduces microcapsule diameters. The term fluid shear as used herein refers to the amount of force exerted by the fluid convection in one solution on a second solution that is in contact with that solution. The term low shear as used herein means a fluid shear force of less than about 100 dynes/cm$^2$. Preferred shear forces are less than about 20.5 dynes/cm$^2$ and more preferred are shear forces of about 12 dynes/cm$^2$ or less. It can be appreciated that the shear forces decrease as the distance between the fluid interface increases. Thus, in a typical method the shear forces may vary from about 20.5 dynes/cm at a distance of 30 microns from the fluid interface to 3.55 dynes/cm$^2$ at a distance of 0.1 cm from the interface. These estimates of shear forces are based on calculations that assume the fluid interface acts as a wall and that the fluids are incompressible and immiscible. The term gravity as used herein is meant to include conditions of unit (1–g) gravity that are found on Earth.

The terms multi-layered and multi-lamellar are used interchangeably and refer to the fact that the microcapsules of the invention comprise at least two layers. In some instances, the core layer will be hydrophobic in nature and will be completely surrounded by at least one neighboring hydrophilic layer. In other instances, the core layer will be hydrophilic in nature and will be completely surrounded by at least one hydrophobic layer. It is not necessary that the present invention that layers alternate between hydrophobic and hydrophilic. For example, a hydrophilic aqueous layer could be surrounded by a hydrophilic layer containing polyvinyl pyrrolidone.

The present invention provides a method for preparing microcapsules that involves formulating two solutions, a primary solution and secondary solution. The method involves adding the primary solution to a first chamber and adding a secondary solution to a second chamber. The second chamber is immediately adjacent to the first chamber and is separated from the first chamber by a porous barrier. The porous barrier has a pore size of less than the diameter of the desired microcapsules. The second solution is added to the second chamber so as to create an interface with the first solution at the porous barrier. The solutions are allowed to become quiescent, meaning that there is a minimum convective flow between them. After allowing the solutions to become quiescent, typically for a period of ten seconds, the interface between the quiescent solutions is moved away from the porous barrier. Microcapsule formation begins spontaneously as the interface moves away from the porous barrier. Microcapsule formation is allowed to continue for between five minutes to two hours after which, in certain methods, microcapsules are collected by filtration through a porous barrier. This porous barrier may be the same barrier that separates the two solutions but this is not required. Devices are envisioned in which a second porous barrier is used to collect the microcapsules.

The basic method of the invention relies on liquid-liquid interactions. In the basic method, the first step entails formulating a primary solution which will make up the microcapsule shell. The second step entails formulating a secondary solution which will form the microcapsule core. The two solutions are formulated so that they form an interface when they are in contact. Dissolved gas can be removed from the solutions of the present method but this is not necessary.

In one method used to produce a hydrophilic microcapsule core surrounded by a hydrophobic shell, a hydrophobic primary solution is formulated by combining at least one compound from each of the following groups: an organic solvent, a polymer, a co-solvent, an oil, and water. The first solvent typically is about 75–90% by volume of the primary solution. The first polymer is selected to be one soluble in the solvent and typically will comprise about 1–5% by volume of the first phase by volume. A small amount of a co-solvent is also added to the primary solution. This co-solvent may function as a co-surfactant. Oil comprising about 1–10% by volume is also added to the formulation. The first phase may also contain about 1–10% water by volume. The primary solution may serve as a carrier for chemical additives such as pharmaceuticals or other bioactive compounds or commercially desirable compounds that can be used to modify the characteristics of the microcapsule in desirable ways. These additives can be added up to their solubility in the primary solution. Suitable formulations of hydrophobic primary solutions can be prepared by reference to Table I. The organic solvent of the hydrophobic primary solution may be selected from the group shown in Table I. Isopropyl alcohol is preferred. The polymer of the primary hydrophobic solution is selected to be one soluble in the organic solvent selected and may be selected from the group of polymers consisting of glycerol monostearate, glycerol monooleate, glycerol monolaurate, and their mixtures. For example, a mixture of 85–90% glycerol monostearate and 10–15% glycerol monolaurate can be used. Glycerol monostearate is the preferred polymer. Alternatively, glycerol dioleate, glycerol distearate, cholesterol, stigmasterol, phytosterol, campesterol, and lecithins such as phosphatidyl cholines and the like can be used.

TABLE I

FORMULATION OF HYDROPHOBIC PRIMARY SOLUTION

| Solvent (75–90%) | Polymer (1–5%) (monoglycerides) |
|---|---|
| ethyl alcohol | glycerol monolaurate |
| methyl alcohol | glycerol monostearate |
| isopropyl alcohol | glycerol monooleate |
| | mixtures of monoglycerates |
| | (polyglycerides) |
| Co-solvent (0–20%) | glycerol dioleate |
| $C_3$–$C_8$ alcohols | glycerol distearate |
| Tetrahydrofuran (THF) | (sterols) |
| dioxane | cholesterol |
| acetonitrile | (plant sterols) |
| dimethylformamide (DMP) | stigmasterol |
| dimethyl sulfoxide (DMSO) | campesterol |
| | phytosterol |
| Water(1–10%) | (phospholipids) |
| | lecithins |
| Oil(1–10%) | phosphatidyl choline |
| (unsaturated or saturated) | |
| iodinated poppy seed oil (IPO) | myverol 1804 (Eastman Kodak) |
| mineral oil | vitamin E succinate |
| cotton seed oil | |
| olive oil | Dissolved Chemicals to saturation as desired |
| safflower oil | |
| canola oil | |
| peanut oil | |
| sesame oil | |
| corn oil | |

The present method also involves formulating a hydrophilic secondary solution which is encapsulated by the polymer of the primary solution. The hydrophilic secondary solution comprises at least one of each of the following: a solvent, a polymer soluble in the secondary solution, a surfactant, and a salt. By hydrophilic it is meant that the present secondary solutions are hydrophilic relative to the primary solutions. The relative, approximate volume percentages of these constituents is about 70–98% solvent, 1–10% polymer, 1–4% surfactant, and 1–3% salt (by weight). Suitable formulations of the hydrophilic secondary solution can be prepared by reference to Table II. The solvent of the secondary solution is typically water. The polymer, surfactant and salt of the secondary solution are typically chosen from the groups listed in Table I. The secondary solution also serves as a carrier solution for chemical additives such as pharmaceuticals or other bioactive or commercially desirable compounds which can be added to the secondary solution up to the solubility limit of the compounds.

TABLE II

FORMULATION OF HYDROPHILIC SECONDARY SOLUTION

| Solvent (70–98%) | Polymer (1–10%) |
|---|---|
| Water | Polyethylene glycol (PEG 400–20000) (polysaccharides) MW 4000–100000 |
| Surfactant (1–20%) (HLB > 15) | polyvinylpyrrolidone (PVP) |
| Sorbitan monooleate plus ethylene oxides | polyvinyl alcohols |
| Dextran | polyvinyl acetate |
| PEG | (hydrocolloids) |
| $C_{12}$–$C_{20}$ fatty acids | gelatin |
| quaternary $NH_4$ salts | gum tragacanth |
| ethoxylated salts | carrageenans |
| 2-amino-2-methyl-propanol | karaya gum |
|  | guar gum |
| Salt (1–3% weight/volume) | (alginates) |
| NaCl | (celluloses) |
| KCl | carboxymethyl cellulose |
| $CaCl_2$ | hydroxyethyl cellulose |
| Quaternary ammonium salts | hydroxypropyl cellulose |
| cetyl trimethylammonium bromide |  |
| Phosphate buffered saline (PBS) | Dissolved chemical |
| 4-methoxy-4(3-phosphatidyl choline) spiro (1,2-dioxetane-3,-g,1-adamantane) disodium salt | (to saturation as desired) |

Alternative methods are also contemplated which are useful in the production of microcapsules having a hydrophobic inner core surrounded by a hydrophilic shell. In this method, a hydrophilic primary solution is formulated to contain at least one of each of the following: a solvent (such as water), a cosolvent, a polymer, and oil. Suitable formulations for the primary solution for this method can be prepared by reference to Table III below. As shown, the hydrophilic primary solution typically contains between 70% to about 90% water. In these formulations, the polymer of the hydrophilic primary solution is soluble in that solution and may be selected from the group of polymers shown in Table III.

TABLE III

FORMULATION OF HYDROPHILIC PRIMARY SOLUTION

| Solvent (70–90%) | Hydrophilic Polymer |
|---|---|
| water | polyvinylpyrrolidone (PVP) |
|  | polyvinyl alcohols |
| Co-solvents (0–20%) | polyvinyl acetate |
| $C_3$–$C_8$ alcohols | propylene glycol |
| tetrahydrofuran (THF) | (hydrocolloids) |
| dioxane | gelatin |
| acetonitrile | gum tragacanth |
| dimethylformamide (DMF) | gum arabic |
| dimethyl sulfoxide (DMSO) | gum accancia |
|  | carrageenans |
|  | karaya gum |
| Oil (1–10%) | guar gum |
| iodinated poppy seed oil (IPO) | (alginates) |
| mineral oil | (celluloses) |
| cotton seed oil | carboxymethyl cellulose |
| olive oil | hydroxypropyl cellulose |
| safflower oil | carboxypropyl cellulose |
| canola oil | hydroxyethyyl cellulose |
| peanut oil | (phospholipids) |
| sesame oil | (lecithins) |
| corn oil | phosphatidyl choline |

TABLE III-continued

FORMULATION OF HYDROPHILIC PRIMARY SOLUTION

|  | (polysaccharides) |
|---|---|
| Dissolved compounds | corn starch |
| (to saturation as desired) | cyclodextrins |
|  | dextrans |

In these methods a secondary solution is formulated. Typically, this solution is hydrophobic relative to the primary solution. The hydrophobic secondary solution is formulated to contain at least one of each of the following: a solvent, a cosolvent, a polymer, a surfactant, a salt and the secondary solution can be formulated with dissolved chemical compounds up to their solubility limits. Suitable secondary solutions may be formulated by reference to Table IV.

TABLE IV

FORMULATION OF HYDROPHOBIC SECONDARY SOLUTION

| Solvent (75–90%) | Polymer (1–10%) |
|---|---|
| methyl alcohol | glycerol monostearate |
| ethyl alcohol | glycerol monooleleate |
| isopropyl alcohol | glycerol monolaurate |
|  | mixtures of monoglycerates |
| Co-Solvent | (polyglycerides) |
| $C_3$–$C_8$ alcohols | glycerol dioleate |
| Tetrahydrofuran (THF) | glycerol distearate |
| Dioxane | (sterols) |
| Acetonitrile | cholesterol |
| Dimethylformamide (DMF) | plant sterols |
| Dimethyl sulfoxide (DMSO) | stigmasterol |
|  | campesterol |
| Surfactant (1–20%) (HLB > 15) | phytosterol |
| Sorbitan monooleate plus ethylene oxides | (phospholipids) |
|  | lecithins |
| Dextran | phosphatidyl choline |
| PEG |  |
| $C_{12}$–$C_{20}$ fatty acids | Salts (1–3%) |
| quaternary $NH_4$ ethoxylated salts | NaCl |
| vitamin E succinate | KCl |
|  | $CaCl_2$ |
| Dissolved Chemicals | quaternary ammonium salts |
| (to saturation as desired) | cetyl trimethylammonium bromide |
|  | 2-amino 2-mehyl propanol |
|  | PPD |
|  | Phosphate buffered saline (PBS) |
|  | 4-methoxy-4(3-phosphatidy (choline)spiro(1,2-dioxetane-3-g, 1 adamantane) disodium salt |

In order to ensure that the liquid-liquid interactions necessary to form the microcapsule are present, certain of the constituents of each phase are selected relative to one another. Thus, in one method the surfactant in the hydrophilic secondary solution is selected such that it will have a hydrophilic/lipophilic balance (HLB) value greater than that of the polymer constituents of the primary and secondary solutions. Generally in this method, the most useful surfactants are nonionic and have a HLB value of 10.0 or greater. More preferred are surfactants with an HLB of 15 or more. Sorbitan monooleate with 40 moles of ethylene oxide is the preferred surfactant in this method. Certain HLB values of materials are provided below in Table V.

TABLE V

HYDROPHILIC/LIPOPHILIC BALANCE (HLB) (McCutcheon 1979)

| Compound | HLB |
| --- | --- |
| Glycerol trioleate | 0.8 |
| Cholesterol | 1.0 |
| Triglyceride of coconut oil | 1.4 |
| Sorbitan trioleate | 1.8 |
| Sorbitan tristearate | 2.1 |
| Glycerol monooleate | 2.7 |
| Mono and di glycerides of fatty acids | 2.8 |
| Glycerol Monostearate (GMS) | 2.8–5.0 (3.8 preferred) |
| Propoxylated ethylene diamine plus ethylene oxide | 3–28 |
| Mono/diglyceride | 3.2 |
| Glycerol mono coconut ? ? ? | 3.4 |
| Mono/diglyceride | 3.5 |
| Propylene glycol mono fatty acid ester | 3.5 |
| Monoethoxyl lauryl ether | 3.6 |
| Stearyl lactyl acid | 3.8 |
| Hydrogenated cottonseed oil | 3.8 |
| Sodium lauryl sulfate | 4.0 |
| Mono and diglycerides of citric acid or lactylic ester or fatty acid | 4.2–4.6 |
| Ethoxylated fatty amine (2 moles ETO) | 4.5 |
| Diethylene glycol monostearate | 4.7 |
| Sorbitan monopalmitate | 4.7 |
| Diethylene glycol monostearate and oleate | 4.7 |
| Ethoxylated (2) cetyl ether | 5.3 |
| Glycerol Monoricinoleate | 6.4 |
| Glycerol monolaurate | 6.8 |
| Triglycerol mono stearate | 7.0 |
| Polyethylene glycol (400 dioleate) | 7.2 |
| Lanolin sterol | 8.0 |
| Ethoxylated nonyl phenol (CO-420 & CO 850) | 8.0–16.0 |
| Polyethylene glycol (400) distearate | 8.2 |
| Sorbitan monolaurate | 8.6 |
| Ethoxylated sorbitan fatty acid esters and alkyl/aryl alcohol | 9.0 |
| Anhydrous lanolin | 10.0 |
| Polyethylene glycol monostearate | 11.0 |
| Polyethylene glycol 400 | 11.2 |
| Ethoxylated (10) cetyl ether | 12.9 |
| Ethoxylated GMS | 13.1 |
| Sorbitan monostearate | 14.9 |
| Sorbitan monooleate with 20 moles ethylene oxide | 15.0 |
| Ethoxylated (20) oleyl ether | 15.3 |
| Ethoxylated (20) stearyl cetyl ether | 15.8 |
| Ethoxylated castor oil | 18.0 |
| Nonyl phenol polyethylene glycol ether | 18.1 |
| Polyethylene glycol 600 mono laurate | 19.6 |
| Sodium lauryl sulfate | 40 |
| Propylene glycol monostearate | 40 |
| Hydroxylated lanolin sodium oleyl sulfate | 42 |
| Blends of GMS and sorbitan monooleate with 20 moles ethylene oxide | 52 |

The formulation of the primary solutions of the present methods includes a cosolvent which may be selected from the group of co-solvents having relatively low dielectric constants. Suitable co-solvents include $C_3$–$C_8$ alcohols, tetrahydrofuran, dioxane, acetonitrile, dimethylformamide, dimethylacetamide, and dimethyl sulfoxide and the like. $C_6$ and $C_7$ primary alcohols are preferred cosolvents.

The formulation of the primary solutions of the present methods also includes an oil(s). Suitable oils are unsaturated oils such as poppy seed oil, olive oil, peanut oil, sesame oil, cotton seed oil, soybean oil, safflower oil, corn oil, sunflower seed oil and canola oil or saturated oils such as mineral oil, long chain paraffin oils, liquid petrolatum and the like. In certain preferred embodiments, microcapsule formulations include compounds that assist in imaging so that microcapsules can be located within the body to facilitate treatment. For example, iodinated poppy seed oil (IPO) is incorporated into microcapsules as a marker for tracking the presence of the microcapsule via radiocontrast detection methods. In this method the iodinated poppy seed oil is incorporated in the formulation of the primary solution.

The second polymer, the surfactant and the salt formulated with the secondary solution may each be selected from a particular group of such compounds. The second polymer may be selected from the group of polymers consisting of polyethyleneglycol 400–20000 daltons (Da), dextran ranging from 4000 to 100,000 in molecular weight more preferably 40,000 to 70,000 molecular weight, polyvinyl pyrrolidone, polyvinyl alcohols, polyvinyl acetate, gelatin, gum tragacanth, carrageenan, Karaya gum, Guar gum, gum arabic, alginates, carboxymethyl cellulose, hydroxypropyl cellulose, carboxypropyl cellulose, lecithins and the like. Although the terms polymer and surfactant are used in the Tables with distinct compositions, it is the case that roles of a composition may overlap. For example, mono and diglycerides may also serve as surfactants and ethoxylated quaternary ammonium salts may also serve as surfactants. Similarly, phosphatidyl choline may serve as both a polymer and salt.

In the methods and formulations described previously several principles are involved in the formulations of the primary and secondary solutions. First, the polymer having the lowest HLB value forms the polymeric skin around the microcapsule. This polymer is selected so that it is insoluble in the solution making up the microcapsule core. Suitable polymers of the primary and secondary solutions are selected relative to each other so that they are not soluble in each other, do not react with each other and such that the polymer having the higher HLB value is only approximately soluble in the primary solution. Approximately insoluble means that the composition will not dissolve to a concentration of more than 1% by weight of the solution.

In certain formulations the polymer of the primary solution has an HLB and is of a chemical type such that it is both insoluble in the second solvent and attracts oil and/or the second polymer which has a molecular weight in the range of approximately 200 to 10,000 Da. Such polymers have a hydrocarbon chain length of 12 carbon atoms or larger. Formulations of this type are shown in Example IX, Table X, formulation 1. Table X makes reference to the critical components of the formulations without providing a comprehensive list of each ingredient. For example, pharmaceutical compositions and oils are also incorporated into that formulation but are not specifically referenced. Considerations for selecting those components are as described above. In certain embodiments and methods the polymer that forms the outer skin is selected so that it will dissolve in physiological body fluids. Suitable polymers for this purpose include polyethylene glycol, polyvinyl alcohol, polyvinyl chloride, cellulose acetate, lecithin, gum arabic, gum karaya, gum tragacanth, sodium alginate In an alternative method Example IX, Table X, formulation 3 is an example of a formulation that can be used to produce a microcapsule having an outer, aqueous insoluble, polymeric skin which encapsulates an oil layer that also has a polymeric skin encapsulating an aqueous layer. To produce such a composition the polymer of the primary solution is selected so that it is insoluble in water. The solvent of the primary solution also has an HLB value that is lower than the HLB of the second polymer and has a chain length that tends to attract oil.

Certain methods of the present invention provide for the incorporation of pharmaceutical compositions into microcapsules. In these methods, the pharmaceutical composition is introduced into at least one of the solutions used to formulate the microcapsule layers. In some cases, the additive is introduced at near saturating conditions such that it crystallizes after microcapsule formation. Multi-layered microcapsules of the present invention having hydrophobic and hydrophilic drug compartments enable diffusion of hydrophobic and hydrophilic drugs from the same microcapsule, e.g. antibiotics and immuno-stimulants to treat resistant infections or multiple fibrinolytic drugs to dissolve emboli. The incorporation of pharmaceutical compounds in microcapsules produced by the present methods is described in more detail in the parent patent, U.S. Pat. No. 5,827,531, which is specifically included herein by reference.

The microcapsules of the invention and methods for producing them are of particular utility when formulating organic-soluble drugs as these types of drugs are otherwise very difficult to administer. The pharmaceuticals may be those selected from the group of such widely diversified pharmaceutical compositions as cytotoxins, proteases, cytokines, anti-nauseants, steroids, anti-fungal agents, fibrinolytic enzymes, and antibiotics. The inventors have successfully encapsulated representatives of these classes of pharmaceuticals using the methods of the invention.

In certain preferred embodiments, microcapsule formulations include compounds that assist in the imaging. In addition to iodinated poppy seed oil, which was described previously, magnetic resonance contrast agents can also be incorporated in microcapsules. Examples of such compounds are the metallo-organic compounds including aqueous soluble ferrous gluconate, gadolinium diethylene triamine pentaacetic acid and hydrocarbon-soluble, iron pentacarbonyl and other insoluble contrast agents, e.g. $Fe_3O_4$.

In one method of the present invention, the primary and secondary solutions are formulated and then stored in separate and distinct compartments that are each connected to opposite regions of a central diffusion chamber. Each compartment is configured such that it can deliver its resident liquid into one or the other of the regions of the diffusion chamber.

The basic method of the present invention generally involves creating an interface between the primary and secondary solutions. To this end, the two solutions are brought together in a manner that keeps fluid shear low and that does not alter the adsorptive surface properties at the solution interface. Although this can best be achieved in microgravity where buoyant fluid convection is absent and diffusion-driven fluid convection predominates, it can be accomplished under conditions of gravity by reducing the differences in densities between the two solutions used to form microcapsules and by mechanical methods that reduce fluid shear forces.

One mechanical method for reducing fluid shear is to position a porous barrier in the microcapsule formation chamber such that it separates the chamber into two regions. One solution is introduced into one region through an inlet port, and the other solution is introduced into the other region through a separate inlet port. The porous barrier acts to stabilize the interface between the solutions by suppressing fluid motion.

Such a porous barrier may be composed of either a hydrophobic or a hydrophilic material. It is preferred that this characteristic matches that of the secondary solution, which will make up the core of the desired microcapsules. The reason for this preference is that a thin film of liquid typically wets the porous barrier. When the barrier is hydrophobic the liquid film coating the barrier is hydrophobic. This situation is preferred where microcapsules have hydrophilic outer shells because the outer shell does not tend to adhere or dissolve in the solvent that coats the barrier. Thus, when the desired microcapsules have hydrophilic outer skins, secondary solution is hydrophobic the porous barrier is preferably composed of a hydrophobic material such as polyurethane, polyethylene, polypropylene, nylon, fluorinated polyethylene and the like. Likewise, when microcapsules having hydrophobic outer skins are made, hydrophilic barriers are preferred. Examples of hydrophilic porous barriers are ceramics, glass, polyvinyl acetate and cellulose filters. In certain circumstances a barrier made of cellulose acetate may be used. This material is an intermediate material having both hydrophobic and hydrophilic characteristics and can be wet by either type of solvent. Another consideration in the selection of a suitable porous barrier is its pore size. The porous barrier is selected so that its average pore size is no larger than approximately ½ of the diameter of the desirable microcapsules.

It is preferable to add the secondary solution to the first region so that the porous barrier will be wet efficiently. Subsequently, the primary solution is added to the opposing region. When the invention is practiced under conditions of gravity, it is preferred that the porous barrier be positioned such that it lies in the plane of the interface between the primary and secondary solutions.

After the solutions have been introduced into their respective regions and have become quiescent, the interface between solutions is gently separated from the porous barrier. At this point, spontaneous formation of microcapsules near the solution interface can occur. In some cases, fluid motion is provided to create a controlled amount of fluid shear. This fluid shear can induce microcapsule formation or can be used to reduce the diameters of the microcapsules. In either case, the fluid shear force at the interface is limited to less than 100 dynes/$cm^2$. This controlled low-shear approach to microcapsule formation yields more spherical microcapsules having a desirable size distribution.

Critical to the success of the methods of the invention is the substantial limitation of mixing between solutions phases to diffusion-driven convection. One manner in which to so limit other types of mixing is to carry out the methods under microgravity. Microgravity is defined as a gravity force of less than $1 \times 10^{-3} \times g$. Such gravitational environments may be achieved in a variety of ways, at least some of which are detailed herein. For instance, microgravity may be achieved in certain trajectories of sounding rockets. Even longer periods of microgravity may be obtained with temporary orbiters such as the space shuttle. Relatively indefinite periods of microgravity may be obtained in permanent or temporary orbital spacecraft such as the orbital space station and other geosynchronous orbital satellites. The exposure of the first and second liquids to microgravity has been found to be effective in forming the microcapsules of the invention where the exposure is at least 20 seconds in duration. Certainly, as described more fully below, greater exposure periods are also used. Typically, under conditions of gravity the exposure period ranges from five minutes to about two (2) hours.

Once formed the microcapsules are gently collected. Collection may be by filtration through a membrane filter. In certain methods and embodiments the porous barrier that separates the chambers of the device may also serve as a filter, and may be used to collect newly formed microcapsules. Considerations for selection of the filter are similar to those for selecting the porous barrier. Preferably the filter material is hydrophobic where the outer microcapsule skin is hydrophilic and hydrophilic when the outer microcapsule skin is hydrophobic. In addition, the average filter pore size is no longer than approximately one half of the diameter of the desired microcapsules.

Typically, collected microcapsules are washed to remove residual quantities of the primary solution. If not removed from the microcapsule preparations, the primary solution has a tendency to redissolve the outer microcapsule membrane. The wash step typically involves resuspending microcapsules in a solution that is immiscible with the outer microcapsule membrane. In the case where an aqueous core is encapsulated by a hydrophobic layer, the wash can be with an aqueous solution such as water, a dextran solution with 1% NaCl, a lightly buffered saline solution, the secondary solution and the like. Where microcapsules have a hydrophilic outer shell, they are preferably washed with a hydrophobic solvent such as the solvent of the secondary solution, the secondary solution, cosolvent, oils and the like. After the microcapsules are resuspended they are collected again. Such a wash step has the additional advantage of toughening or curing the microcapsule skin.

The present invention also contemplates methods wherein the washed and collected microcapsules are resuspended in a storage solution, isolated and stored until use. The considerations relevant to selection of suitable storage solutions are the same as for the wash solution. One solution that makes a particularly suitable storage solution is the secondary solution used to form the microcapsules. Use of this solution prevents changes in solute concentrations in the microcapsule core that is caused by solute diffusion down their concentration gradients. Once microcapsules are resuspended in a storage solution they can be removed to a storage chamber by any conventional means.

TABLE VI

STORAGE SOLUTION FORMULATIONS

| HYDROPHOBIC FORMULATIONS | HYDROPHILIC FORMULATIONS |
|---|---|
| Oil (up to 100%) | Aqueous solutions containing: |
| Iodinated poppy seed oil (IPO) | immunoglobulins |
| Mineral oil | albumin |
| Cotton seed oil | gelatin |
| Olive oil | hydrocolloids |
| Safflower oil | polysaccharides |
| Canola oil | - starches |
| Peanut oil | - cyclodextrins |
| Sesame oil | |
| Corn oil | Polymers |
| Paraffins | glycerol monostearate |
| ($C_{14}$–$C_{60}$) | glycerol monooleleate |
| | glycerol monolaurate |
| Polymers | mixtures of monoglycerates |
| glycerol monostearate | (polyglycerides) |
| glycerol monooleate | glycerol dioleate |
| glycerol monolaurate | glycerol distearate |
| mixtures of monoglycerates | (sterols) |
| (polyglycerides) | cholesterol |
| glycerol dioleate | plant sterols |
| glycerol distearate | stigmasterol |
| (sterols) | campesterol |
| cholesterol | phytosterol |
| plant sterols | (phospholipids) |
| stigmasterol | lecithins |

TABLE VI-continued

STORAGE SOLUTION FORMULATIONS

| HYDROPHOBIC FORMULATIONS | HYDROPHILIC FORMULATIONS |
|---|---|
| campesterol | phosphatidyl choline |
| phytosterol | |
| (phospholipids) | |
| lecithins | |
| phosphatidyl choline | |

In certain methods microcapsules may be subjected to electrophoresis. The present invention specifically contemplates methods of electrophoresis of microcapsules including free fluid static column zone electrophoresis, density gradient isoelectric focusing. This method can be used to separate and purify microcapsules, and/or to collect microcapsules and to gently free them from surfaces to which they may adhere. To facilitate electrophoresis a microcapsule formation chamber is fitted with electrodes. Suitable electrode metals include the noble metals and palladium in particular. An electrophoresis solution is formulated and added to a zone of collected microcapsules so as not to disperse them into the solution. Next an electric field sufficient to cause electrophoretic migration of the microcapsules is applied to the chamber. Suitable electric fields range from about 2 V/cm to about 500 V/cm. To collect microcapsules, electrophoresis solution is removed from the chamber and collected in aliquots as the microcapsules reach the end of the chamber. Generally, any solution that does not destabilize microcapsules and that limits electric current flow is suitable for use in the free fluid zone electrophoretic method. Suitable electrophoresis solutions can be prepared by reference to Table VII. In certain methods electrophoresis solutions are supplemented with various compounds such as glucose, sucrose, sorbitol, glycine and the like to make them isoosmotic with the aqueous phase within the microcapsule.

Certain limitations are important to the success of the present electrophoresis methods. Specifically, for free fluid electrophoretic methods the conductivity of the electrophoresis solution is kept below 0.5 mmho/cm. Use of a solution having a low conductivity allows the use of field strengths of up to 500 volts/cm without a large current. The electric current is limited such that less than 0.2% of the ions are converted to $H_2$ or $CL_2$ gas. Generally, currents in the present method are limited to less than 25 milliamps and more typically are in the range of 15 to 20 milliamps. It is important to avoid heating of the electrophoresis solution during electrophoresis because thermal convection reduces separation efficiency. These parameters are also important because they limit the amount of gas produced during electrophoresis. Gas production is deleterious because gas tends to coat the electrodes and obscure the current entering the solutions. The rate of microcapsule migration in free fluid zonal electrophoresis is defined by the equation $v=(\zeta\epsilon/4\pi\eta)E$.

Methods are also contemplated for density gradient isoelectric focusing. The electrophoresis solution in this method is a solution having a conductivity of less than 1.5 mmho/cm, for example, 2.5 mM potassium phosphate, 1% ampholines (LKB) and a density gradient made of 0–20% ficoll (MW 400,000 Pharmacia) or 0–8% sucrose. In this method typical electric field strengths are in the range of 4–6 volts/cm with a resulting current of 15 to 20 milliamps. The rate of microcapsule migration in such a method is defined by the equation $dx/dt=2a^2g(\rho-\rho_0(x))/\phi\eta(x)$. Further details regardin electrophoresis of microcapsules can be obtained generally from Todd, P., (1990), p. 539–672

TABLE VII

ELECTROPHORESIS SOLUTIONS

| | |
|---|---|
| 150 mM NaCl | 145 mM NaCl, HEPES |
| 23 mM triethanolamine, | 11 mM NaCl, 300 mM dextrose |
| 216 mM glycine | 15 mM NaCl, 15% Ficoll |
| 7.5 mM Potassium Acetate, | 1 mM HEPES |
| 27 mM sucrose | 67 mM Na/PO4, |
| 0.5 M sorbitol | 2 mM NaPO$_4$, 6.42 mM NaCl, |
| 10 mM Tris (hydroxymethylamino) methane, 285 mM sucrose | 0.336 mM EDTA, 222 mM glucose, (630 mM DMSO or |
| 2.5 mM sodium propionate | 540 mM glycerol) |
| 0.3 mM hydrogencarbonate, 145 mM NaCl | 10 mM KPO$_4$, 2.65 mM KCl, 0.48 mM MgCl$_2$, 55 mM glucose, |
| 2 mM barbital | 199 mM sucrose |
| 0.3 mM Tris (hydroxymethylamino) methane, 9 mM triethanolamine, | 1 mM KPO$_4$, 2.65 mM KCl, 0.48 mM MgCl$_2$, 55.5 mM |
| 9 mM potassium acetate, 0.0025 mM MgCl$_2$, CaCl$_2$, 5 mM | glucose, 199 mM sucrose 0.65 mM triethanolamine, 30 mM |
| glucose, 285 mM sucrose | glycine, 0.3 mM MgCl$_2$, |
| 0.3 mM Tris (hydroxymethylamino) methane, 0.3 mM boric acid | 0.027 mM CaCl$_2$ 2.25 mM potassium phoshate, |
| 2.5 mM sodium barbital pH 8.3, | pH 7.2 |
| 2.5 mM potassium phosphate, 6.42 mM NaCl, 0.367 mM KH$_2$PO$_4$, | 0.2 mM potassium acetate, 220 mM glycerol, 44 mM sucrose |
| 1.76 mM Na$_2$HPO$_4$, 222 mM glucose, 0.336 mM Na$_2$EDTA | |
| 0.1 Grams/liter triethanolamine, 2.07 mM glycine, 0.02 potassium acetate, 0.006, < MgCl$_2$, 0.004 mM CaCl$_2$, 2.0 mM glycerol, 1.5 mM sucrose | |

The present invention contemplates methods for adding additional layers or coatings to microcapsules. These layers may be used to provide a protective coating around the microcapsule, to modify the net surface charge of a microcapsule, to modify the rate that solutes diffuse out of the microcapsule, and/or to add useful chemical species in the outside of the microcapsule. Layers are added by suspending microcapsules in a coating solution that contains a coating molecule. Suitable coating solutions can be formulated by reference to Table VIII, which provides representative compositions that can be used to form coatings on microcapsules.

In some methods a coating solution is formulated with an oil or $C_{20}$–$C_{60}$ paraffin and the solution placed in contact with microcapsules. In such instances, a waxy paraffin coating will surround the microcapsule and the predominant forces holding the layer together are Van der Waals forces. In other instances, the methods involve formulating a coating solution comprising charged polymers and contacting microcapsules with this solution. In such methods, a coating forms around the microcapsule that is primarily driven by electrostatic interactions. The basic method and alternatives are summarized below.

Whether used in conjunction with a one-layer microcapsule or with microcapsules with more than one layer, the coatings of the present invention are of substantial utility. The coatings can be either substantially of a hydrophobic nature or of a hydrophilic nature as described below. They may be derived from addition of certain polymers in the initial formulations of the liquids used to make the microcapsules or can be added in a separate coating step. Where hydrophobic coatings are used in conjunction with drug-delivery systems, the coatings are selected for their complementary permeability to the drug to be delivered. The polymers are also selected for their flexible characteristics after formation and curing which is of particular utility during intravascular transport and allows higher packing densities for forming emboli such as in chemoembolization therapy. Thus, for example where a water-soluble drug is to be delivered, the drug is contained in an inner aqueous layer over which is placed a coating permeable to the dissolved drug. Preferably, the coating material should be impermeable to solvents or oils. The coatings which have been observed to be deposited on the surfaces of the microcapsules of the invention are about 0.01–2.0 microns thick where the coating is a hydrophobic coating, and about 0.1–5.0 microns thick where hydrophilic coatings are deposited.

TABLE VII

COATING COMPOSITIONS

| Anionic coatings | cationic coatings | zwitterions |
|---|---|---|
| Polyvinyl pyrrolidone | polyhistidine | phosphatidyl choline |
| Polyvinyl acetate | polylysine | dipalmityl |
| Phosphatidyl serine | polyarginine | phosphatidyl |
| Phosphatidyl glycerol | stearylamine | choline |
| beef heart cardiolipin | protamine | cyclodextrins |
| fibronectin | trypsin | aminobutyric acid |
| laminin | lysozyme | amphoterics |
| collagen | glycoproteins | ampholytes |
| Egg phosphatidyl choline | chitosin | |
| Halogenated phosphatidyl choline | gelatin PEG-8000 pH 8.5 | |
| Alkylsulfonate | polycationic | |
| Chitosin | protamine sulfate | |
| Succinylated chitosin | fibronectin | |
| Gelatin | cetylpyridinium | |
| Polyglutamic acid | chloride | |
| Polylactic acid | vancomycin | |
| Polyhydroxymethyl-methacrylate/polyamine | | |
| Polygalactose | | |
| bees wax | | |
| carnuba wax | | |
| PEG 8000 pH 7.0 | | |
| Dicetylphosphate | | |
| serum proteins | | |
| heparin | | |
| protamine | | |
| alkylsulfonates | | |
| serum peptides | | |
| alginates | | |
| polyanionic protamine sulfate | | |
| succinylated poly-L-lysine | | |
| vancomycin | | |

Compounds disclosed in Table VIII can be used to impart specific characteristics in microcapsules. For example, using polycations, such as polyarginine, to coat the surface of microcapsules decreases membrane fluidity and can be used to reduce the rate of solute diffusion through the membrane. Stearylamine coatings can be used to improve targeting of microcapsule payloads to certain body organs such as the liver. Vancomycin coatings can be prepared to allow microcapsules to selectively bind anionic chiral enantiomers. Similarly, type I collagen coatings are useful in the preparation of microcapsules targeted to the ventral neural pathways, while laminin or fibronectin coatings can be used to restrict microcapsules away from the ventral pathways of the brain.

Coatings may be used to add pharmaceutical compositions to the formed surface of the microcapsule. Instances of this include coating with immunoglobulins, other proteins, hydrocolloids or polysaccharides. These coatings may be particularly useful for producing microcapsules with unique immunologic, proteinaceous, surface charge, or other surface characteristics which makes them selectively adhere to certain target tissues (cells), or renders the microcapsules less or more attractive to certain phagocytic immune cells (e.g. when these cells are the actual target for the therapeutic drug). Where the coating is a hydrocolloid, it may be selected from the group of such hydrocolloids consisting of collagen, isoelectric gelatin, agar, gum arabic, gum tragacanth, alginates, cellulose derivatives and carrageenans. In some instances the coating fluid comprises an oil or $C_{14}$–$C_{60}$ paraffin for coating the formed microcapsules. Regardless of what coating material is desired, the material typically is dissolved or suspended in a solution having a low ionic strength such as electrophoresis solutions or in water.

Coating compositions may also contain a chemical activator which can act on inactive forms of the pharmaceutical agents such as proteins (drug) as they diffuse out of the microcapsule. This is illustrated when the pharmaceutical is a pro-enzyme and where the activator is another proteolytic enzyme which cleaves the pro-enzyme at active site to render the molecule biologically active. This embodiment can be used to deliver very labile drugs which have very limited shelf-lives or short biological half-lives and can maximize the therapeutic effectiveness of the short-lived drug at the target site of action.

In a preferred coating method, an electric field of approximately 10 to 40 volt/cm is applied to the to the microcapsule/coating solution suspension. In this method it is absolutely necessary for the solvent containing the coating composition to have a conductivity of less than 1.5 mmho/cm. Suitable solutions are the electrophoresis solutions of listed in Table VII. Typically, the coating composition is dissolved in the solvent to a concentration of at least about 0.1% to about 0.5% by weight. The electric field is applied such that the coating composition migrates through the chamber containing microcapsules. As the coating composition contacts the microcapsules it sticks to the microcapsules through electrostatic interactions and forms a protective coating around them. In this manner the coating compositions can be electrostatically deposited on the surface of the microcapsule to form a polymeric coating around the microcapsules. Unexpectedly, the inventors found that this electrostatic coating process can be used to coat microcapsules having either a net positive or a net negative surface charge with either cationic or anionic polymers.

In a preferred electrostatic microcapsule coating method microcapsules are placed in a solution containing 0.1% to 0.5% polyvinyl pyrrolidone (PVP) in water or in the primary solution and an electric field of 10 Volts/cm applied to the suspension. In such a method the PVP diffuses through the solution and coats microcapsules having a positive surface charge. Alternatively, polyvinylacetate can be used as the coating material in analogous methods.

Thus, in certain methods and compositions of the invention, a multi-layered microcapsule will be produced which comprises at least three layers or phases. When the first layer is an aqueous layer or core, the next layer may be an organic layer. This organic layer may then be suspended in an aqueous solvent containing a coating material. The coating material then forms a polymeric skin over the outer surface of the hydrophobic shell. Conversely, the liquid at the core of the microcapsule may be an organic liquid encapsulated by an aqueous layer. Such a microcapsule can be coated by a coating material dissolved or suspended in an organic layer. The microcapsules are then suspended in the organic solution containing the coating solution and the coating material forms a skin around the aqueous shell. Extension of these basic formulations are also envisioned where additional layers are possible or where multiple skins or coatings are desired.

The microcapsules prepared by the present methods, due in one regard to their being constructed with outer polymeric coatings, are particularly flexible yet rugged (able to withstand shear forces greater than 10 dynes/cm$^2$). As will be related specifically below, microgravity experiments, on sounding rockets (1989–92) and Shuttle missions STS-52 (1992) and STS-56 (1993) using an automated Materials Dispersion Apparatus, produced multi-lamellar microcapsules containing both Cis-platinum (anti-tumor drug) and iodinated poppy seed oil (a non-radioactive, radiocontrast medium), surrounded by a polymeric skin. Microcapsules formed with amoxicillin (antibiotic) or urokinase (a blood clot dissolving enzyme), co-encapsulated with IPO, remained intact for over two years after their return to earth.

Once layers are added, microcapsules can be suspended in storage solution and collected as described previously. In other methods microcapsules can be isolated by electrophoresis as described. Microcapsules having a net charge can be collected by electrophoresis. This is easily accomplished by placing an electrode of the appropriate charge in the microcapsule formation chamber near an outlet port. An electric field sufficient to cause electrophoretic migration of the microcapsules is applied to the chamber. Typically, such fields are in the range of 10–40 V/cm. Microcapsules are collected by removing the liquid near the electrode and depositing it into a storage vessel as the microcapsules migrate toward the electrode.

Also provided with the present invention is a microencapsulation and electrostatic processing device for forming microcapsules. In one embodiment, the device comprises a chamber having a filter, which separates a first region in the chamber from a second region in the chamber. An aqueous solution is introduced into the first region through an inlet port, and a hydrocarbon solution is introduced into the second region through another inlet port. The filter acts to stabilize the interface and suppress mixing between the two solutions as they are being introduced into their respective regions. After the solutions have been introduced and have become quiescent, the interface is gently separated from the filter. At this point, spontaneous formation of microcapsules at the interface may begin to occur, or some fluid motion may be provided to induce microcapsule formation. In any case, the fluid shear force at the interface is limited to less than about 100 dynes/cm$^2$. This low-shear approach to microcapsule formation yields microcapsules with good sphericity and desirable size distribution.

In one embodiment, the microencapsulation device relies on liquid-liquid interactions for microcapsule formation. Two solutions are brought together to form an interface in such a mechanical manner that the fluid shear properties are controlled to low levels, below about 12 dynes/cm$^2$, and such that the adsorptive surface properties at the immiscible interfaces are not significantly altered. Although the exact mechanisms are not fully understood, the inventors believe that the maintenance of certain surface properties, such as the surface tension, Helmholtz charge distribution (electrical double layer), and partitioning of surfactant molecules between two immiscible fluids must remain substantially intact so that lateral phase separation can occur in a manner which allows simultaneous formation of multiple liquid interfaces (oil/water or water/oil) and which results in microcapsules having alternating spherical shells of hydrophilic and hydrophobic liquid layers. This is believed to be the mechanism for the formation of multi-lamellar vesicles which are formed in a single step. Although this can best be demonstrated under microgravity conditions, wherein buoyant convection is absent and diffusion-driven convection predominates, microcapsule formation can also be accomplished in unit gravity conditions by balancing the density differences between the two fluids or by mechanical means which prevents excess fluid shear from significantly altering the normal adsorptive surface properties which are determined by the chemical composition of the fluids and the interfacial phenomena among their solvents, polymers and surfactants.

In one implementation, the two solutions are allowed to interact at their interface without agitation, stirring, shearing or like force, and even quiescent forces such as gravity-controlled sedimenting, shifting, and drift are limited. Thus, in this implementation only chiefly diffusion-driven convection is used to spontaneously form microcapsules, as the chemical formulations of the different fluids assist in lowering the surface free energy across the interface. As the microcapsules form, a polymeric outer coating is created.

As shown in the parent patent, U.S.Pat. No. 5,827,531, the methods of the present invention result in more spherical microcapsules of varied size ranges. When comparing certain prior art equipment and methods for forming microcapsules (Microfluidics, Inc.), the inventors found that even the preferred formulations of the invention were incapable of providing such uniformity. In certain instances, hardly any microcapsules formed at all where mixing and vortexing were used to distribute one phase into the next. In others, poorly formed and non-spherical microcapsules resulted. In contrast, the methods of the present invention were successfully used to generate uniform, spherical microcapsules. This uniformity allows facile sieving or filtering of the microcapsule products in order to obtain highly uniform diameter fractions. importantly, the methods of the invention allow the formation of larger-sized, multi-lamellar microcapsules (1–350 micron) than heretofore possible.

Methods and embodiments are provided in the present invention that allow microcapsule formation, collection and washing within a single closed chamber. Microcapsules may be washed by introducing a wash solution into the chamber containing the microcapsules. The wash solution is generally immiscible with the outer layer of the microcapsule. In one method the wash solution is comprised of the solvent mixture that makes up the hydrophilic core of a microcapsule. Alternatively, water or phosphate buffered saline solutions may be used.

Methods are also provided for coating microcapsules with protective polymeric coats using an electrostatic coating process. One such method involves placing the microcapsules in a coating solution consisting of approximately 0.1% to 0.5% polyvinyl pyrrolidone dissolved in a solution having a high resistance to current flow. An electric field of approximately 10 volts/cm is applied to the solution such that the polymer molecules migrate through the first chamber and coat the microcapsules. The present methods are not meant to be limited to the application of a single polymeric coating and methods are contemplated for repeating the coating steps so that multiple coatings are applied to microcapsule.

Certain methods of the present invention include supplying a controlled amount of fluid shear to the solution interface during microcapsule formation. This step facilitates microcapsule formation in certain circumstances such as under conditions of gravity. The amount of fluid shear is kept below 100 dynes/cm$^2$. In certain methods the shear is applied by allowing solution to flow into the chamber where microcapsules are forming.

Micrcocapsules can be collected by isolating them in a coating solution by means well known in the art. However, an alternative method for isolating charged microcapsules is to move the microcapsules through an electric field into a collection zone near an outlet from the chamber and then remove them to a collection chamber. Embodiments of the present invention are contemplated wherein an electrode is positioned inside the microcapsule formation chamber to facilitate the electrophoretic collection of microcapsules in this chamber.

BRIEF DESCRIPTION OF THE DRAWINGS

FIGS. 2–15 are schematic illustrations of the steps in the microcapsule formation process.

DETAILED DESCRIPTION OF THE INVENTION

Figure 1:
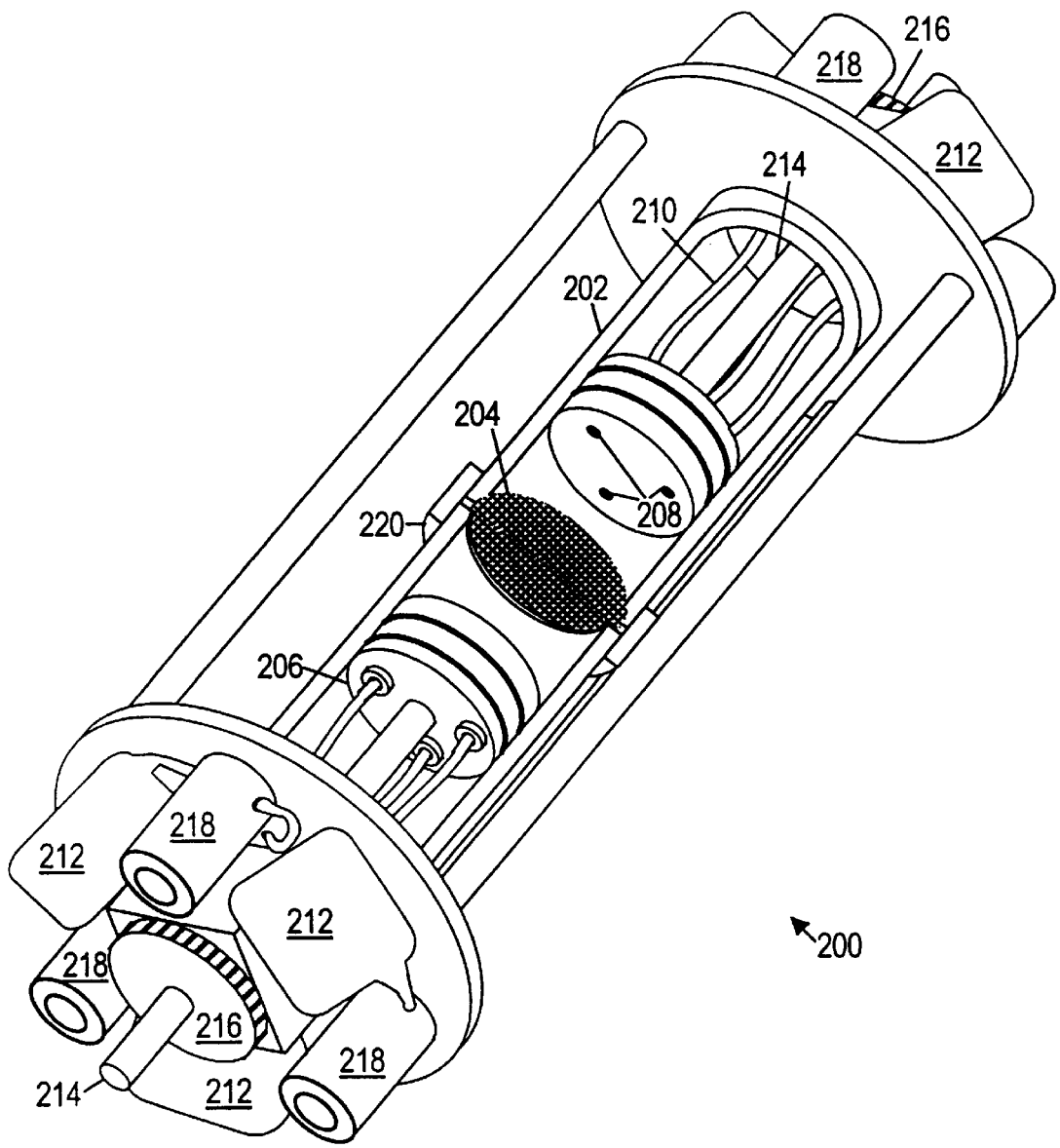
FIG. 1 illustrates one embodiment of a microencapsulation and electrostatic processing device.

A series of more than 38 separate experiments on four space flights has led to the development of this invention. These experiments along with their ground-based counterparts are described below for the purpose of pointing out the invention specifically and providing details useful in carrying out the invention. These specific examples, however, do not limit the scope of the claimed invention.

A multi-lamellar microcapsule may have an aqueous layer/drug (such as cis-platinum) at its center, a hydrocarbon/oil drug and/or radiocontrast medium (e.g. IPO) as a next layer, and a polymeric outer skin. To form such a microcapsule, a hydrocarbon solution and an aqueous solution, are brought together to form an interface with minimal mixing and low shear. If diffusion-driven convection is allowed to occur at the interface thereafter, microcapsules having two layers will begin to form.

EXAMPLE I

MICROGRAVITY EXPERIMENTS SUMMARY

Microencapsulation-related experiments designed to produce microcapsules under conditions of microgravity were conducted on six space missions beginning in April 1989 with the Consort-I sounding rocket using the Materials Dispersion Apparatus (MDA) mini-lab developed by Instrumentation Technology Associates, Inc. The sounding rocket flights produced only 6.5 minutes of microgravity conditions, but this was adequate to form the unique microcapsules in a single step. Experiments on the Space Shuttle permitted 10 minute dispersion times followed by curing of the outer polyglyceride skin for eight days under microgravity conditions. A summary of these experiments is shown in the following table. New formulations were tested on Shuttle STS-52, using only aqueous-soluble drugs, polymers and surfactants, and on STS-56 using alcohols as co-surfactants. The specific experiments and results are described in detail in the examples to follow.

TABLE IX

MED Flight Experiments Summary

| MISSION | DATE | EXPERIMENTS | MATERIALS | RESULTS |
|---|---|---|---|---|
| Consort-1 | 4/89 | Protein diffusion | urokinase & antibodies | diffusion rates established |
| Consort-1 | 3/90 | Diffusion kinetics | urokinase & myoglobin | kinetics verified |
| Consort-4 | 11/91 | Microencapsulation of drugs[a,b] | Cis-Platinum, amoxicillin, urokinase & Strept-avidin | multi-lamellar microspheres w/alternating hydrophilic & hydrophobic layers |
| Consort-5 | 9/92 | Microencapsulation of drugs[a,b] | Cis-platinum, amoxicillin & urokinase | multi-lamellar microspheres w/alternating hydrophilic & hydrophobic layers |
| STS-52 | 10/92 | Microencapsulation of drugs (aqueous polymers only)[a,b] | Cis-platinum, amoxicillin & urokinase | multi-lamellar microspheres, crystals within microcapsules |
| STS-56 | 4193 | Microencapsulation of drugs (alcohol co-surfactants)[a,b] | Cis-platinum, amoxicillin & urokinase | multi-lamellar microspheres, crystals within microcapsules |

[a]Fluorescent labels included
[b]Fluorescent beads included

EXAMPLE II

GRAVITY-DEPENDENT RESTRICTIONS RECOGNIZED

Gravity-dependent restrictions in the basic liquid-liquid spontaneous microencapsulation process led to the design of several microgravity experiments to explore the utility of this process when density-driven phenomena were eliminated. In particular, density-driven, gravity-dependent restrictions of the liquid-liquid microencapsulation process were: early phase separation producing fragile microcapsules; interfacial dynamic flow causing coalescence of microcapsules. Failure of ground-based experiments to derive uniform microcapsules lead to a desire to attempt microcapsule formation in space.

The microgravity flight experiments led to the development of a new liquid-liquid microencapsulation process that involves use of surfactants and co-surfactants in the aqueous phase and co-surfactant alcohols in the organic phase, which also contained, in one embodiment, high molecular weight polymers that formed a tough outer "skin" on the final microcapsules. In microgravity, a single step dispersion produced unique multi-lamellar microcapsules containing various aqueous drugs co-encapsulated with iodinated poppy seed oil (a radiocontrast medium with a sp. gravity= 1.35). Subsequent ground control experiments also produced some of these unique microcapsules and illustrated that the 1×g process could be improved to yield useable microcapsules by using different formulations. In particular, it became clear that the outer coatings substantially improved the ruggedness of the microcapsules formed.

EXAMPLE III

SOUNDING ROCKET EXPERIMENTS

Initial experiments on Consort-1 and -3 were used to determine the effective mixing and diffusion kinetics of solutions in the MDAs. This showed that sufficient volume was mixed at the interface via diffusion to allow formation of microcapsules. These experiments also provided the diffusion constants for each of the components of the liquid phases.

The first successful microencapsulation of drugs in microgravity was conducted on the Consort-4 mission in November 1991. The microcapsules were recovered and analyzed by microscopic image analysis. Mono-dispersed fluorescent beads were included as internal size standards and fluorescent labels were used to determine the distribution of drug in the various fluid compartments. Additional experiments, conducted on Consort-5 in September 1992, confirmed the capabilities of the new method for forming multi-lamellar microcapsules with alternating layers of hydrophilic and hydrophobic drugs.

Microcapsules formed in 38 microgravity mini-experiments used liquid-liquid dispersion of aqueous drug solutions, surfactant and polyethylene glycol dispersed in alcoholic co-surfactant solutions containing soluble polyglycerides.

Microcapsules of both oil/water and polymer/water/oil were recovered from the Consort flights. These experiments produced multi-lamellar liquid microcapsules (concentric spheres within spheres) comprised of three or more, alternating immiscible layers. Image analysis of the microcapsules was made possible by co-encapsulation of standard size fluorescent beads. Microcapsules were formed in the ranges of 1–15 microns, 40–50 microns, 110–130 microns and 160–230 microns in diameters. This was a substantial improvement over prior art approaches that produce microcapsules of less than 10 microns. The size distribution covered a range of from about as low as 5 microns in diameter up to about 300 microns in diameter and greater. The average size of the microcapsules formed in the present experiments was about 150 microns, greatly in excess of the average 10 microns or less diameters obtained with prior art approaches.

The ruggedness of the microcapsules formed under these conditions allowed for size segregation by sieving. Digital analysis of phase contrast and fluorescent images taken with a fluorescent microscope confirmed that the aqueous-soluble drugs were routinely encapsulated within the inner aqueous core and the outermost aqueous shell of the microcapsules.

Multi-lamellar microcapsules containing large amounts of IPO (Guerhart Laboratories—France, Savage Laboratories—U.S.A.) in discrete lamella have been prepared. Microcapsules can be heavily loaded with IPO, containing up to 38% of the total microcapsule volume with IPO. Often small hemispheres of IPO were also found clinging to the outer surface of the large inner (aqueous) sphere or adhered to the outer polymer skin of the microcapsule.

Microcapsules formed by almost all of the formulations survived 15+g accelerations, severe vibrations and turbulent mixing, during the reentry of the experiment capsule, and have remained intact for two years after recovery from space. These multi-layered microcapsules were similar to liquid-filled, thin-skinned, micro-balloons which were flexible enough to be manipulated on a microscope slide without collapse.

The microcapsules formed in just 6.5 minutes of microgravity retain their spherical shape and appeared tough enough to survive the extensive physical manipulations required for sizing, final preparation and storage of parenteral suspensions, and the fluid shear encountered after intravascular injection.

Also formed were very unusual structures (multiple small spheres of aqueous-soluble drug) distributed within multi-lamellar o/w/o microcapsules, wherein the aqueous spheroids are arranged in an annular ring that appears fixed in a plane within the innermost sphere (not shown). These ring structures remain intact when the microcapsules are "rolled around" on the microscope slide without rupturing. These structures demonstrate the ability of the methods of the invention to form small spheroids that do not coalesce inside the larger microcapsule. Such structures may be advantageously used to control the specific volume to surface area ratio in order to control the rate of diffusion of a solute in such spheroids. In particular, sustained release of pharmaceuticals contained in such spheroids within microcapsules may find utility.

EXAMPLE IV

SPACE SHUTTLE EXPERIMENTS

Microencapsulation experiments on Consort 4 and Consort 5 used mixtures of aqueous-soluble drugs, IPO, $C_3$–$C_8$ alcohols and polyglycerides that were insoluble in aqueous solutions. In experiments conducted on STS-52, the inventors co-encapsulated cis-platinum (diaminodichlor-cis-platinum; Bristol Laboratories) with IPO by forming microcapsules from water-soluble polymers using special formulations of aqueous, non-alcoholic solvents. Such formulations will find particular utility in co-encapsulations of anti-tumor compounds along with radiocontrast medium for tracking drugs in the body.

Polyvinyl pyrrolidone (PVP) and a commercial lecithin (CENTROLEX-F™ by U.S.Soya, Inc.) were used to form multi-lamellar microcapsules at 20° C. Fluorescent beads and fluorescent labeled were co-encapsulated with the drugs to permit drug-distribution measurements, within the various lamellae, using fluorescence microscopy and digital image analysis at the NASA Johnson Space Center, Houston, Tex. The final microcapsules were suspended and recovered in aqueous solutions, IPO or mineral oil. The microcapsules formed by these formulations were similar to those made using alcohol-soluble polyglycerides. However, without the hydrocarbon soluble polyglyceride skin these microcapsules were more fragile.

Another unique type of microcapsule was formed during these experiments that was characterized by drug crystals formed within the inner aqueous core of the multi-lamellar microcapsules. Microcapsules with 65% of their central aqueous compartment occupied by crystals of Cis-platinum have been observed. Microcapsules containing crystals of amoxicillin were also formed in the STS-52 experiments. These illustrate that aqueous-soluble drugs can be encapsulated at very high concentrations near the solubility limit of the drug. After the microcapsules are formed the drug can be further concentrated through dehydration of the microcapsule. This dehydration process leads to crystal formation within the microcapsule. One result of this process is that the dissolved drug, which is typically more stabile in crystalized form can be stored for more prolonged periods.

Microcapsules formed from first organic solvent/polymer methods appeared to be more rugged (by visual comparison under the microscope) than those formed on STS-52 formed from first solvent aqueous/polymer methods. The STS-56 experiments again produced multi-lamellar liquid microcapsules (multiple concentric spheres within spheres) comprised of alternating layers. Using fluorescent 6.4 micron beads and image analysis, it was found that the most interesting microcapsules were formed in the range of 10–15 micron, 40–50 micron, 50–100 micron, and 160–230 micron diameters. These diameter distributions were of particular interest since it is known that intraarterial uses can accommodate 50–300 micron diameter microcapsules while intravenous applications can only tolerate 1–10 micron microcapsules. Thus, by segregating the microcapsules into sized fractions (sieving), it should be possible to address particular intravascular limitations.

As noted above, microcapsules were formed containing crystals of cis-Platinum or amoxicillin. The crystals apparently were formed after encapsulation. Several microcapsules were formed that contained a single, large cubic crystal of cis-Platinum, which so completely filled the inner sphere that only about 15% of the inner volume remained as a liquid. One encapsulated, cubic Cis-Platinum crystal was measured at 48 microns across within a 57 micron diameter microcapsule. After formation, some of the microcapsules were dispersed in an external oil phase (either IPO or mineral oil) and allowed to cure for eight days before return to Earth.

These microgravity experiments have shown that formation of multi-lamellar, alternating-phase microcapsules can be controlled by proper timed-sequence exposures of the immiscible phases using special solvent formulations and surfactants. Once formed, these microcapsules remain spherical due to the predominant surface tension of the internal phases and polymer/solvent phase partitioning at the interfaces.

These experiments clearly demonstrated the capability to use liquid-liquid diffusion and low fluid shear mixing to form unique microcapsules containing hydrophilic and hydrophobic drugs under microgravity conditions. Thus, ground-based experiments were conducted to compliment and replicate the space experiments. These ground-based experiments were able to replicate the size range (5–250 microns in diameter) to a limited degree, but the average size microcapsule obtained was about 10–40 microns in diameter. Still, this was a substantial improvement over the prior art approaches that rarely formed microcapsules over 10 microns in diameter. It was also observed that the ground-based experiments resulted in less rugged microcapsules. This is likely a result of the gravity-dependent deformations of the spherical microcapsules as they form giving rise to areas of thinner polymer deposition. Thus, the flexible microcapsules, formed under microgravity conditions, have more uniform size distributions than those formed in 1×g, are more rugged, and have a higher average diameter than ground-made microcapsules, largely due to the absence of thermal convection, buoyancy forces, and instabilities that occur at the solution interfaces.

The microgravity experiments illustrate the feasibility of co-encapsulating aqueous-soluble drugs, hydrocarbon-soluble drugs and oil-based contrast media within a lipid-soluble, polyglyceride outer film which cures rapidly enough to be impervious to oil or hydrocarbon resolubilization. They also allow the formation and harvesting of unique microcapsules which are durable enough to be removed from the external solvent without disruption or destruction of the internal phases. It is anticipated that these microcapsules will have several advantages over conventional liposomes that are designed for intravascular injection.

EXAMPLE V

DISCUSSION AND ALTERNATIVE EMBODIMENTS

Spontaneous formation of multi-lamellar, microcapsules containing alternating layers of aqueous and hydrophobic solvent compartments is strongly dependent on the interfacial tension and the amount of mixing between solutions. On Earth this process is limited by gravity-dependent, density-driven separation of the solutions into stratified horizontal layers. In microgravity, this process is largely dependent on the surface-free energies of the different liquids independently of density-driven convection and separation. Hydrocarbon soluble, high molecular weight polymers have been included in the formulations to form flexible, permeable "skins" or outer coatings around the liquid microcapsules as they are created by phase partitioning mechanisms. It is also possible to form such polymer barriers between internal layers. The microcapsules can be formed and cured without deformation by contact with container walls.

More specifically, co-encapsulation of an aqueous-soluble, anti-tumor drug (Cis-platinum) and a radio-contrast medium (IPO), in microgravity, has produced a unique drug delivery system that can be visualized by radiologic or computerized tomography scanning to insure that the cytotoxic drug is delivered directly to the target tumor. Multi-layered microcapsules have been developed which can provide a new intravascular delivery system for targeted tissues and sequential, sustained release of multiple anti-tumor drugs. This method has resulted in formation of flexible spherical microcapsules of more uniform sizes, which can provide maximum packing densities and maximum drug delivery to target organs or tumors.

Multi-layered microcapsules can be designed to protect active forms of urokinase and other thrombolytic enzymes until they are delivered and entrapped at the local site of a blood clot, where therapeutic doses of the enzyme can diffuse out to dissolve the unwanted embolism. These methods also could be used for encapsulating certain labile drugs to make microcapsules for special purpose drug delivery systems, especially those designed to deliver drugs via the nasal or buccal mucosa or via inhalation directly to the lungs. Examples include protected delivery of mucolytic DNAse for sustained release treatment of cystic fibrosis and I anti-trypsin for patients with deficiencies in the lung epithelium.

EXAMPLE VI

REDISPERSION OF MICROCAPSULES IN AQUEOUS OR OIL VEHICLES

A frequently used step includes dispersion of the microcapsules (after they have formed) in different aqueous/polymer solvents or in a pure oil phase. A unique attribute of microcapsules formed by these methods is that they do not re-dissolve in an oily external phase, even when the semi-permeable outer skin is hydrophobic. This produces a suspension in the liquid carriers that are commonly used for intravascular administration.

EXAMPLE VII

EXEMPLARY FIRST ORGANIC SOLVENT MICROCAPSULE FORMULATIONS

The following formulations have been used with particular success by the inventors in both earth normal and microgravity methods of making microcapsules.

The microencapsulation procedure begins with the formulation of two liquid solutions that form an interface when they contact each other. Tables I and III provide guidance on formulating the primary solution, which primarily form the microcapsule skin, and Tables II and IV provide guidance on formulating suitable secondary solutions, which primarily form the microcapsule core.

Primary Solution—(hydrocarbon). The solvent is a hydrocarbon fluid (ethyl alcohol, methyl alcohol, or isopropyl alcohol) with a low or medium HLB (HLB=5–10). One or more co-solvents are used (which also can act as co-surfactants). Small concentrations of oil and water are added. Into this mixture, the mono- or polyglyceride is dissolved up to 5% w/v. An example is:

88% isopropanol 2.5% m-Hexanol 2.5% n-Heptanol

5% Sodinated poppy seed oil

2% $H_2O$

5% glycerol monostearate

Secondary Solution—(aqueous). The second solvent is water plus surfactants (ex. polyethoxylated sorbitan esters; polyethylene glycol). A polysaccharide (Dextran) and normal saline (0.9%) are added which helps achieve the desired critical micelle concentration. A pharmaceutical soluble in water is added. An example is:

1% PEG 4000

5% Dextran-40 (MW=40,000)

0.9% Sodium chloride

2% Sorbitan Monooleate/20 moles Ethylene oxide

Water (up to 100% volume)

dissolved drug at specified concentration (according to required dose and release rate)

Storage Solution—(oil). An oil, immiscible with the first two fluids in which the microcapsule's "outer skin" is insoluble so that the suspended microcapsules can be delivered by injection when non-aqueous administration is required. Submersion of microcapsules in the oil also can aid the curing or polymerization of the "outer skin." A preferred example of the oil vehicle is iodinated poppy seed oil which also serves as a radiocontrast medium.

Alternate Compositions for Primary Solution

Main solvent—ethyl alcohol

Co-solvents—(co-surfactants) are normal alcohols—$C_3$ to $C_8$ high dielectric constant solvents— tetrahydrofuran dioxane acetonitrile dimethylformamide dimethylacetamide
dimethylsulfoxide Oil—dense radiocontrast liquids such as iodinated poppy seed oil, cotton seed oil, safflower oil, olive oil, canola oil, peanut oil, sesame oil, corn oil.
  saturated oils can be used, such as heavy mineral oil, liquid petrolatum Polymers—used to form the "outer skin" on the microcapsules
  monoglycerides—especially glycerol esters ranging from $C_{12}$–$C_{22}$, e.g. monostearate, distearates, monooleates, monolaurates and olive oil
  polyglycerides—cholesterol, waxy plant sterols (stigmasterol, phytosterol, campesterol)
  phospholipids—lecithins (phosphatydl choline) and/or combinations with mono /polyglycerides Alternate Concentrations:

| Fluid 1: | Main solvent | 75–95% |
|---|---|---|
|  | Co-solvents | 1–10% |
|  | Oil | 1–10% |
|  | Polymer | 1–5% |
|  | Water | 1–20% |

Alternate Composition for Secondary Solution

PEG 200–10000

Dextran-40 (MW=40,000–70,000)

0.9% Sodium chloride

Sorbitan Monolaurate/20 moles Ethylene oxide balance is water

Drug dissolved at saturated or specified concentration (according to required dose and release rate)

Alternate Concentrations:

| PEG | 1–5% |
|---|---|
| Dextran (MW = 40,000–70,000) | 5–10% |
| Sodium chloride | 0.9% |
| Sorbitan Monolaurate/20ETO | 1–5% |
| Water (balance of volume) |  |

Drug concentration saturated or specified

Alternate Composition for Storage Solution (Oils)

Dense radiocontrast liquids s.a. iodinated unsaturated oils e.g. poppy seed oil, cotton seed oil, safflower oil, olive oil, canola oil, peanut oil, sesame oil, corn oil.

Also saturated oils can be used, s.a. heavy mineral oil

Alternate concentrations: 100% oil or a mixture is used as a carrier vehicle for the suspended microcapsules

EXAMPLE VIII

EXEMPLARY FIRST AQUEOUS SOLVENT MICROCAPSULE FORMULATIONS

ALTERNATE METHOD—Hydrophilic Outer Skin

Primary Solution—(aqueous); the main solvent is a water, one or more co-solvents (which also can act as co-surfactants), and a lecithin is dissolved up to 5% w/v to form the outer skin on the microcapsules.

| An example is: | 3% polyvinyl alcohol dissolved in a mixture of |
|---|---|
|  | 20% isopropyl alcohol and |
|  | 80% water |

Secondary Solution (aqueous); the main solvent is water plus surfactants (ex. polyethoxylated sorbitan esters; polyethylene glycol) and plus a polysaccharide (Dextran) and normal saline (0.9%) which helps achieve the desired critical micelle concentration.

| An example is: | 1% PEG 4000 |
|---|---|
|  | 5% Dextran-70 (MW = 70,000) |
|  | 0.9% Sodium chloride |
|  | 2% Sorbitan Monooleate/20 moles Ethylene oxide |
|  | Water (up to 100% volume) |
|  | dissolved drug at saturated or specified concentration |
|  | (according to required dose and release rate) |

Storage Solution (aqueous)—a PEG and PVP solution which can aid the curing or toughening of the "outer skin."

1% Polyvinyl pyrrolidone

4% PEG 4000

5% Dextran-70 (MW=⁻70,000)

balance is 0.9% Sodium chloride

EXAMPLE IX

ADDITIONAL MICROCAPSULE FORMULATIONS

Table X provides a summary of certain key ingredients in the formulations of microcapsules. In particular these formulations provide examples of microcapsule solutions that can be used to form microcapsules having more than two layers. For example, shown in formulation 1 the polymer of the primary solution has an HLB and is of a chemical type such that it is both insoluble in the second solvent and attracts oil and/or the second polymer which has a molecular weight in the range of approximately 200 to 10,000 dlatons. Such polymers have a hydrocarbon chain length of 12 carbon atoms or larger.

Formulation 3 is an example of a formulation that can be used to produce a microcapsule having an outer, aqueous insoluble, polymeric skin which encapsulates an oil layer that also has a polymeric skin encapsulating an aqueous layer. To produce such a composition the polymer of the primary solution is selected so that it is insoluble in water. The solvent of the primary solution also has an HLB value that is lower than the HLB of the second polymer and has a chain length that is tends to attract oil

TABLE X

ALTERNATIVE MICROCAPSULE FORMULATIONS

| | SOLVENT | POLYMER | SURFACTANT |
|---|---|---|---|
| Formulation 1 | | | |
| Primary solution | Hydrocarbon (alcohols) | Insoluble in aqueous solution HLB < 8.0 (Glycerol monostearate, HLB = 4.0) | |
| Secondary Solution | water (with dissolved salt) | Aqueous soluble HLB > 10.0 (PEG 1000) | Aqueous soluble HLB > 12.0 Sorbitan mono-Oleate + 20 ETO, HLB = 15.0 |
| Formulation 2 | | | |
| Primary solution | Hydrocarbon (alcohols) | Insoluble in aqueous solution HLB < 8.0 Sorbitan Monolaurate HLB 7.9 | |
| Secondary solution | Aqueous (water with dissolved salt) | Aqueous soluble HLB > 12.0 (polyoxethylene (10) Lanolin alcohol, HLB = 13) | Aqueous soluble 8.5 < HLB < 12.0 Poly oxethylene glycerol trioleate, HLB = 11 |
| Formulation 3 | | | |
| Primary solution | Hydrocarbon (alcohols) | Aqueous insoluble or partially soluble, 5 < HLB < 10 (glycerol mono-ricinole monolaurate, HLB = 6.4) | |
| Secondary solution | Aqueous (water with dissolved salt) | Aqueous soluble HLB > 10 PEG 400 HLB = 11 | HLB < 5 mixed mono & di-glycerides, HLB 3.5 |
| Formulation 4 | | | |
| Primary solution | Hydrocarbon (alcohols) | Aqueous insoluble, HLB < 8 (glycerol monooleate, HLB = 2.7) | |
| Secondary solution | Aqueous (water with dissolved salt) | Aqueous soluble HLB > 12 PVP HLB = 15 | aqueous soluble 8.5 < HLB < 11.5 polyoxyethylene Sorbitan (4) monostearate, HLB = 9.6 |
| Formulation 5 | | | |
| Primary solution | Aqueous (water/alcohol) | sparingly soluble in aqueous solution 8 < HLB < 12 PEG 400 - distearate, HLB = 8.2 | aqueous soluble 12 < HLB polyoxyethylene Sorbitan (4) monostearate, HLB = 15.3 |
| Secondary solution | Aqueous (water/saline) | aqueous soluble, 10 < HLB < 12 (PEG monostearate, HLB = 11) | |
| Formulation 6 | | | |
| Primary Solution | Aqueous (water/alcohol) | sparingly soluble in aqueous solution 8 < HLB < 10 PEG 400 - distearate, HLB = 8.2 | |
| Secondary Solution | Aqueous (water/saline) | aqueous soluble, 10 < HLB (lanolin) | aqueous insoluble HLB < 6 diethylene glycol monooleate HLB = 4.7 |

EXAMPLE X

METHOD FOR PREPARING MICROCAPSULES

In a preferred embodiment the low-shear microencapsulation and electrostatic process is carried out in a microencapsulation chamber such as that shown in FIG. 1. The device of FIG. 1 consists of two thick glass chambers placed end to end and separated by a gasket and porous barrier 204. Barrier 204 is chosen so that it is porous to the solutions used in microcapsule formation but will not allow microcapsules of the desired diameters to pass through. The chambers are held in place by a support structure. Each chamber contains a moveable plunger 206, driven by a shaft 214 connected to a stepper motor, and three fluid conduits 210, each connected to a solenoid valve, and a separate reservoir. In a typical operation in conditions of gravity the chamber is vertical so that one chamber is directly above the other chamber. Plungers 206 are sealed so that the chamber(s) and fluid circulation components are a closed system, such that movement of a plunger causes pumping of a particular fluid when the valve is open to the reservoir containing that fluid. In the following example there are three (3) separate reservoirs connected to each plunger via individual conduits, for a total of six (6) separate fluid reservoirs. The reservoirs may be pliable bags.

Generally, the method of microcapsule formation involves the steps of filling each chamber with the appropriate formulations for microcapsule formation, layering the solutions next to each other such that they are in contact at the porous barrier, moving the solution interface away from the porous barrier, allowing microcapsules to form under quiescent, low shear conditions, separating the liquid from the microcapsules thereby collecting the newly formed microcapsules, and rinsing the microcapsules to remove residual solvents. In preferred methods, a coating is added to the microcapsule. This is facilitated by suspending the microcapsules in a coating solution and applying an electric field. This causes the polymer molecules to adhere to the microcapsules through electrostatic interactions.

Reference is now made to FIGS. 2–15 for a more detailed description of these methods. FIGS. 2–15 are schematic diagrams that illustrate a sequence of steps that have been used to form microcapsules. Initially, the microcapsule formation chamber is empty. Reservoirs A and D contain the two immiscible fluids that will form the first two layers in the microcapsules. Reservoir B holds a wash fluid, reservoir F holds a coating or suspension fluid, reservoir C is a harvesting reservoir, and reservoir E is a waste reservoir. All valves are closed. When the device is used in the presence of gravity, the device is leveled such that the porous barrier is parallel with the plane of gravity. Of course, when no gravity is present this alignment step is unnecessary. All solutions may have dissolved gases removed by standard methods but this is not necessary to the success of the method.

FIG. 2 shows a first solution contained in reservoir A filling the first chamber, in this example the solution is a primary solution. For the purposes of this description the first chamber is defined as the chamber in which microcapsules are formed and which contains the solution interface. The first chamber is filled by motion of plunger 206 of the first chamber away from the porous barrier 204 (as shown in FIG. 1) while valve A is opened. The next step, as shown in FIG. 3, is to fill the second chamber with a second fluid contained in reservoir D. For the purposes of this description the second chamber is defined as the chamber in which microcapsules are not formed. As shown in FIG. 3, the second chamber is filled by moving of plunger 206 of the second chamber away from porous barrier 204 while valve D is opened. As the second solution from reservoir D is introduced into the second chamber, an interface between the primary and secondary solutions forms at porous barrier 204. The filling steps occur slowly so as to avoid undue agitation of the solution interface. If bubbles appear during the filling process they are removed before microcapsule formation.

Once the filling is complete and bubbles are removed, valve D is closed and the solutions are allowed to become quiescent by allowing the device to rest undisturbed for a period of time sufficient to reduce fluid convection to a minimum. Typically, the solution in reservoir A is a hydrocarbon solution having a lower density than the aqueous solution that is placed in reservoir D. However, the present invention is not limited to this configuration and the inventors have observed microcapsule formation when this order is reversed. In this case the function of reservoirs A, B and C are substituted for D, E and F respectively. Thus, the hydrocarbon solution is in reservoir D, the wash solution is contained in reservoir E, reservoir F is a harvesting reservoir, reservoir B is a waste reservoir, and reservoir C is a coating or suspension fluid reservoir.

FIG. 4 shows the next step in the method, which involves gentle movement of the fluid interface away from the barrier in a manner that does not induce substantial fluid shear. In FIG. 4 the interface is moved into the first chamber by the synchronous movement of pistons. Spontaneous formation of microcapsules begins and is allowed to progress for at least 5 minutes and can be allowed to continue for up to two hours. Useful microcapsules have been formed in less than 20 seconds using this method.

In some methods, particularly under conditions of gravity, microcapsule formation maybe encouraged by instituting a gentle flow of solution across the interface. As shown in FIG. 5, where this step is used, mild fluid shear is created at the solution interface by motion of the plunger in the second chamber away from the porous barrier while valve A is opened. This creates a gentle fluid flow that assists the solutions in "rolling up" to form microcapsules. Obviously this step is terminated before the interface reaches the porous membrane barrier. Low fluid shear is preferred since this results in larger capsules of more uniform size. Therefore, in the present methods fluid shear is limited to less than 100 dynes/cm$^2$ and is preferably less than about 20 dynes/cm$^2$.

Figure 8:
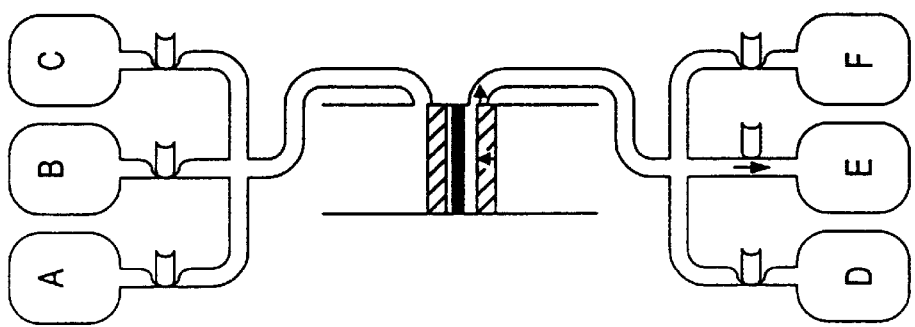
Figure 7:
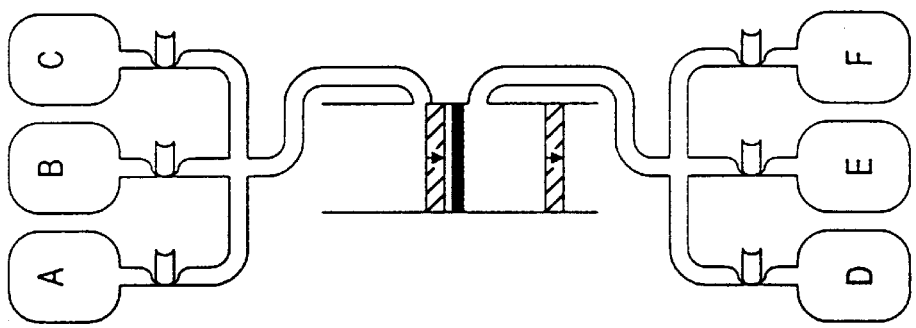
Figure 6:
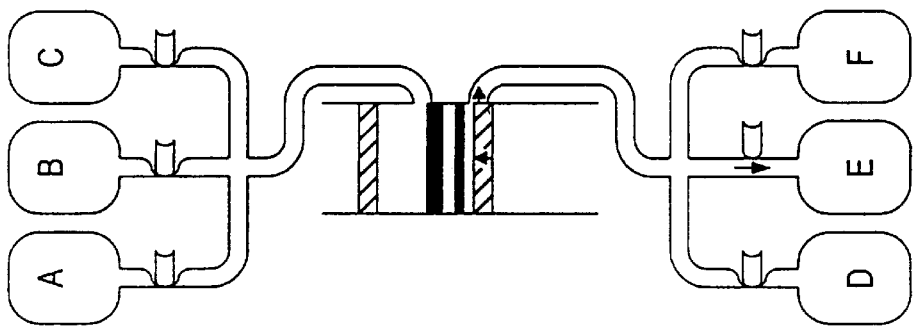
Figure 13:
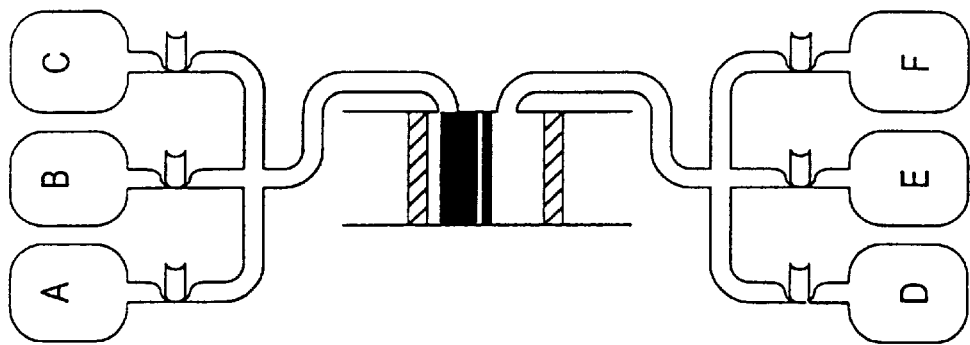

Once microcapsules have formed they are collected. To collect microcapsules the second chamber is emptied into waste reservoir E as shown in FIG. 6. This is achieved by movement of the plunger of the second chamber toward the porous barrier while valve E is opened. As shown in FIGS. 7 and 8, fluid from the upper chamber is then transferred to the waste reservoir by the synchronous movement of both plungers with the plunger of the first chamber moving towards the porous barrier as shown in FIG. 7 followed by movement of the plunger of the second chamber toward the porous barrier while valve E is open as shown in FIG. 8. In this process microcapsules having diameters larger than the pore size of the pores in the porous barrier are collected on the barrier as the solution passes through the barrier and into waste reservoir E.

Figure 9:
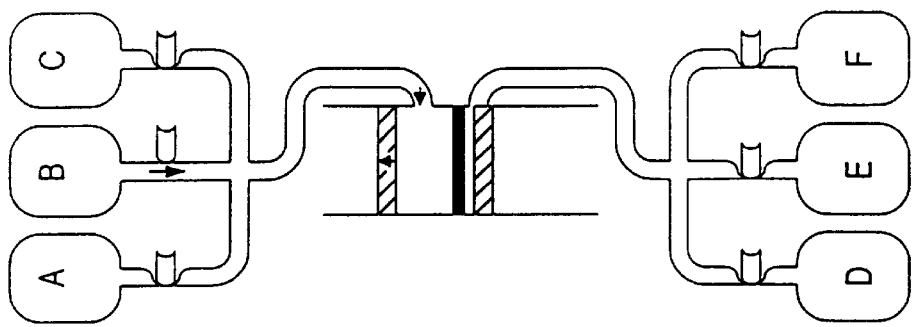
Figure 10:
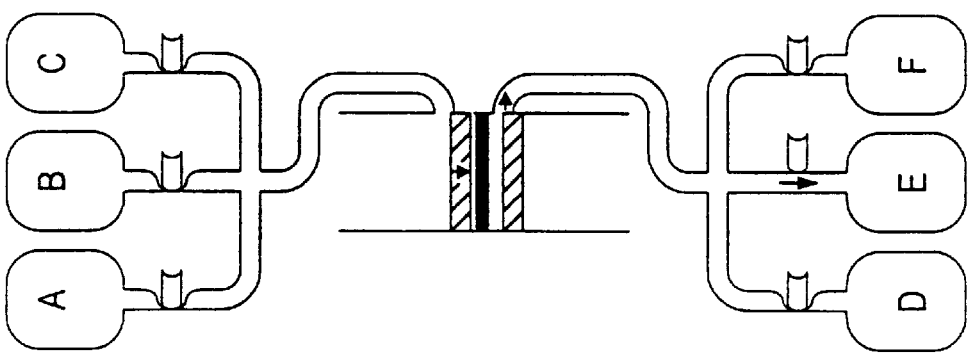

The isolated microcapsules are then rinsed with a wash solution to remove residual unwanted solvents. Suitable wash solutions are generally immiscible with the outer layer of the microcapsules so that the shell is not disrupted by the rinse. The rinse also helps to cure the outer shell. The mechanism of curing is unknown but is defined as the toughening of the outer skin of the microcapsule. One suitable rinse solution is the solution used in the core of the microcapsule. Where the outer layer of the microcapsule is hydrophobic, microcapsules can be rinsed with water, phosphate buffered saline solution, or the like. FIG. 9 shows the filling of the upper chamber with rinse fluid from reservoir B. This is achieved by upward motion of the upper plunger while valve B is opened. The wash solution is removed from the first chamber by movement of the plunger of the first chamber toward the porous barrier while valve E is opened, as shown in FIG. 10. In this process microcapsules are again collected on the porous membrane barrier.

Figure 12:
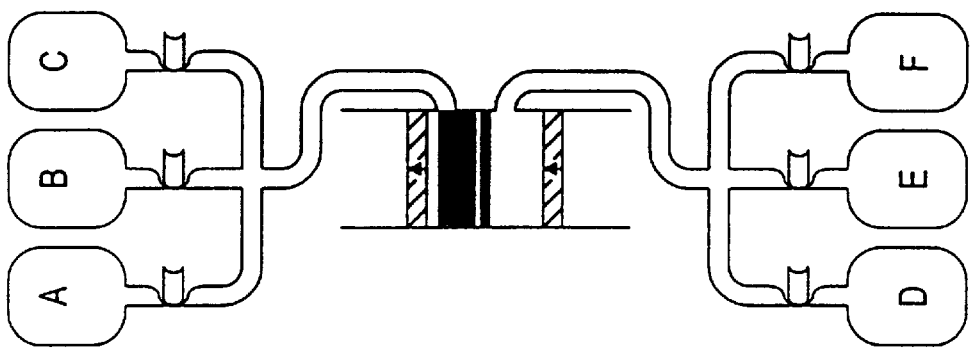
Figure 11:
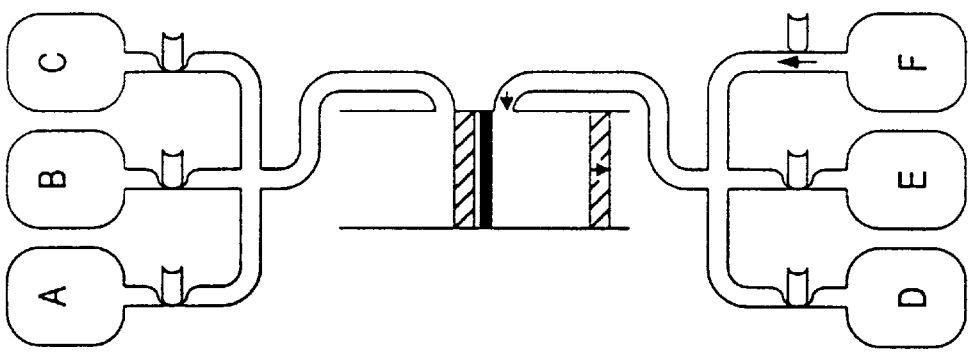

In preferred methods the microcapsules are electrostatically coated with a polymeric coating such as polyvinyl pyrrolidone or polyvinyl acetate or other coating solutions. This coating process greatly strengthens the microcapsules. The coating solution is 0.1% to 0.5% by weight of the polymer in a solvent having high resistance to current flow. One suitable solution is a 0.1% solution of polyvinyl pyrrolidone in water. The coating solution is introduced into the microcapsule containing chamber from reservoir F as shown in FIGS. 11–12. This is achieved by filling the second chamber by lowering the plunger of the second chamber while valve F is open, FIG. 11. Then valve F is closed and the solution in the lower chamber is transferred into the first chamber by synchronous movement of both plungers in the direction of the first chamber, as shown in FIG. 12. This operation lifts the microcapsules from the filter and suspends them in the coating fluid.

Figure 14:
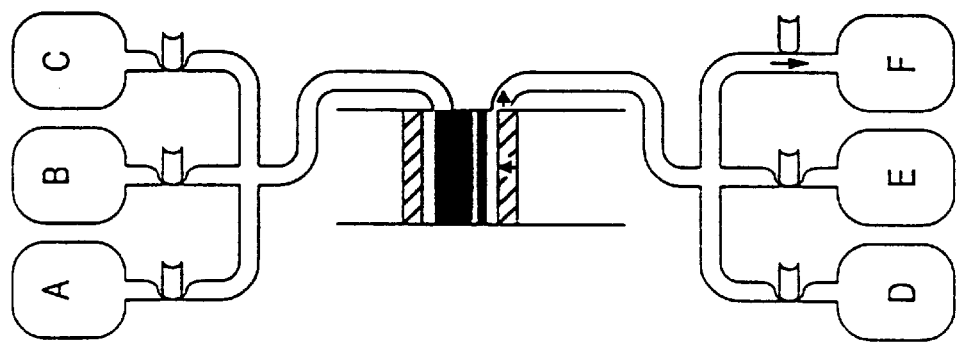

Next, an electric field is imposed on the coating solution containing the microcapsules. This has been accomplished by incorporating electrodes into the plungers. A suitable electric field is 10–40 volt/cm. In methods that involve the use of negatively charged polymeric coating compounds such as polyvinyl pyrrolidone, the cathode is located in the first chamber and the anode is placed in the second chamber so that the polymer molecules will tend to migrate through the first chamber toward the microcapsules. In one method, the voltage is raised in steps to a desired maximum voltage and held for roughly 5 to 15 minutes while the polymer coating forms and completely encapsulates the microcapsule. Upon completion of the coating process, the coating solution in the lower chamber is emptied back into reservoir F by upward motion of the lower plunger while valve F is open as shown in FIG. 14. Surprisingly, this method works to coat microcapsules even when they have a net negative charge. The mechanism by which this coating process works is not known with certainty but the inventors believe that the electric field induces positive charges in the coating molecules which are then attracted to the negatively charged microcapsules.

Figure 15:
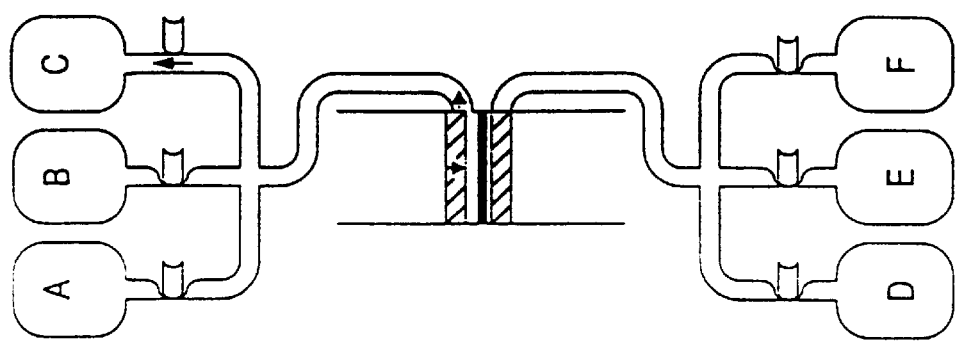

In certain methods, the microcapsules may be collected after completion of the electrostatic coating process. However, additional coatings can be added to the microcapsules either electrostatically or by techniques well known in the art. The microcapsules are collected by movement of the plunger of the first chamber toward the porous barrier while valve C is open as shown in FIG. 15. The coated microcapsules are thereby collected in reservoir C to complete the method.

An alternate electrostatic coating method utilizes slowly alternating DC fields to change the local concentration of charged coating material near the microcapsule surface. In this method the electrostatic field is stepped up to 10–40 V/cm for several minutes, then the voltage is reduced to zero, the polarity of the electrodes is reversed and then the voltage is stepped up again to the previous value. This method has the advantage of reducing the amount of electrolysis and subsequent production of gases caused by electric current flow.

An alternate method for collecting microcapsules is to use an electrostatic field to cause charged microcapsules to migrate toward an electrode of opposite charge. Thus, a device such as the device in FIGS. 2–15 is fitted with an electrode. An electric field induces migration of charged microcapsules toward the plunger in the microcapsule formation chamber where they are removed by pumping out the electrophoresis solution. This technique has several advantages over other collection methods. The technique allows for separation of microcapsules based on their charge and resistance to fluid friction. More highly charged microcapsules will to migrate toward the electrode more quickly than microcapsules having a lower charge. In addition, this process is a gentle means for dislodging microcapsules that become attached to the surfaces of the microencapsulation apparatus.

EXAMPLE XI

OPERATION OF MICROENCAPSULATION ELECTROSTATIC COATING DEVICE

Turning again to FIG. 1, a first embodiment 200 of a microencapsulation device is shown. Device 200 comprises chamber 202, porous barrier 204, plungers 206, inlet/outlet ports 208, tubes 210, reservoirs 212, shafts 214, motors 216, valves 218, and support member 220. Device 200 is configured to create a quiescent, planar interface between two immiscible fluids whereby microcapsule formation occurs in a largely spontaneous manner due to interfacial coacervation. Device 200 is further configured to maintain precise control over fluid flows and fluid shear along the interface. Device 200 may be further configured to concentrate, rinse, coat, flush, and harvest microcapsules after they have formed, all without removing the microcapsules from the original process chamber. The method of operation is discussed further below.

Chamber 202 comprises an inert, preferably transparent, material such as glass or Pyrex®. A cylindrical shape is preferred but not strictly necessary. A porous barrier 204 is positioned transversely within the chamber 202 to separate the chamber into two regions. Porous barrier 204 is preferably a porous membrane filter which is initially used to stabilize the interface between the two fluids, but which may later be used for harvesting microcapsules. For this later use, the filter 204 is provided with a characteristic pore size which will screen larger particles from a fluid flow and allow smaller particles to pass through. Filter 204 preferably comprises inert materials which are non-wetting to the microcapsule's outer coating (i.e. contact angle is less than 90°). Nylon and polypropylene are examples of preferred filter materials.

It is noted that in one embodiment, device 200 rests in a gimbaled assembly which allows 180 degree inversion and at least some horizontal tilt in either direction to facilitate fluid loading and unloading and to assist in removal of air bubbles from chamber 202. In a preferred embodiment, the device is operated in a vertical orientation when in a gravitational field so that the filter 204 is horizontally disposed within chamber 202. Hereafter, references to the "upper plunger" or the "upper region of chamber 202" refer to the plunger and region which would be above filter 204 during processing in a gravitational field. Similarly, references to the "lower plunger" or the "lower region of chamber 202" refer to the plunger and region which would be below filter 204 during processing in a gravitational field.

Chamber 202 is sealed on two ends by plungers 206. The plungers 206 are made of inert materials that are easily machined. For device 200, inlet/outlet ports 208 are provided in the plunger faces, but they may alternatively be positioned on the side walls of chamber 202. The inlet/outlet ports 208 are coupled to fluid reservoirs 212 via flexible tubes 210. The reservoirs 212 may take the form of collapsible pouches, as shown, or they may be provided in the form of syringes, ventilated containers, pressurized cannisters, etc. The number of reservoirs 212 in device 200 may be variable, ranging from at least two to as many as desired. In device 200, the inflow or outflow of fluids will be driven by pressure differentials created by piston-like motion of plungers 206. As is discussed further below, the plungers 206 may additionally be provided with electrodes, pressure transducers, and/or temperature sensors on the plunger faces. The electrodes, pressure transducers, and/or temperature sensors may also alternatively be located elsewhere on the chamber walls or filter surfaces.

The plungers 206 are driven axially in chamber 202 by motors 216 via threaded rods 214. Motors 216 are preferably stepper motors which provide high torque at extremely slow speeds. Shafts 214 are preferably electrically non-conductive. As the motor actuators pivot, they cause shafts 214 to move in or out, which causes the plungers 206 to move correspondingly, thereby displacing fluid into or out of chamber 202. This embodiment allows the upper plunger and lower plunger to be moved independently of each other while the processing chamber and intermediary membrane remain fixed. The upper and lower regions of the chamber together form a closed system, wherein movements of either plunger provide positive or negative pressure on the fluids, so that when one of the valves 218 is open fluids are slowly moved into or out of the chamber 202. The simultaneous, unidirectional movement of the plungers 206, when all valves 218 are closed, serves to move the immiscible fluid interface away from the filter 204.

The various reservoirs may be made accessible or inaccessible to chamber 202 by valves 218. Each reservoir 212 is provided with a valve 218. Valves 218 may be solenoid-driven pinch valves which close the reservoirs by pinching tubes 210. The valves 218 are usually closed, and consequently normally-closed valves may be preferred.

Support member 220 acts as a holder for filter 204 and a sealing gasket which separate the two regions of chamber 202, and may further serve as a coupler for two pieces used to form chamber 202. In this embodiment, filter 204 is a replaceable membrane filter

EXAMPLE XII

MPD ELECTROSTATIC PROCESS USED TO FORM MICROCAPSULES CONTAINING REGLAN WITH OUTER PVP/PEG 4000 COATING

The following procedure was used to generate a microcapsule that was 79 microns in diameter and having a PVP coating that was 8 microns in diameter. The volume of the drug containing solution in the microcapsule was 47.5% of the total microcapsule volume. To produce such microcapsules a primary and secondary solution was formulated. The composition of the primary and secondary solutions was as follows.

| | |
|---|---|
| Primary Solution: | 1 mg/ml Reglan |
| | 1% Polyethylene Glycol-4000 |
| | 5% Dextran-40 |
| | 1% Sorbitan monooleate with 20 moles ethylene oxide (Tween 80) |
| | 0.5% Polyvinyl pyrrolidone (PVP-K90) |
| | 0.05% Cy-3 fluorescent dye |
| Secondary Solution: | 5% w/w Glycerol monosterate (polysaccharide mixture, Eastman 1800) dissolved in the follwoing: |
| | 92% Isopropyl alcohol |
| | 3% Iodinated Poppy Seed Oil |
| | 2% Water |
| | 1.5% Hexanol |
| | 1.5% Heptanol |

Percentages in the formulations indicate weight/volume percentages unless otherwise indicated. The designation mg/ml means milligrams per milliliter. The designation w/w means a weight per unit weight measurement.

The microcapsule was prepared under conditions of gravity by filling the lower chamber of the microcapsule formation device with the secondary solution. Air bubbles that may have entered the device were then removed by tapping the device in an inverted position until the bubbles exited the solution inlet port and were isolated from the chamber. Next the upper chamber of the device was filled with the primary solution. The interface between the solutions was then moved away from the porous barrier into the chamber containing the primary solution. Microcapsules were allowed to form for five minutes. Next an electric field of 14 V/cm was applied to the microcapsule formation chamber for 1 minute. The polarity of the electrodes in the device was reversed and an electric field of 14 V/cm was applied to the microcapsule formation chamber for a period of 30 seconds. Next, the lower chamber of the device was emptied and the microcapsules were collected by forcing the fluid in the upper chamber through the porous barrier/filter. The microcapsules were washed with distilled water. The wash step was repeated and the microcapsules were resuspended in water and collected by moving the upper plunger toward the porous barrier and allowing the microcapsules to exit through an outlet in the plunger to be collected in a storage chamber.

EXAMPLE XIII

FORMATION OF 160 MICRON DIAMETER MICROCAPSULES

The following procedure was used to create microcapsules having a diameter of over 160 microns. Initially a primary and secondary solution was formulated as follows:

| | |
|---|---|
| Primary Solution: | 2.5% w/v Myverol 1804 (Eastman Chemical) |
| | 2.5% w/v Vitamin E Succinate (Eastman Chemical) |
| | 88% Isopropyl alcohol |
| | 5% Iodinated Poppy Seed Oil |
| | 2% Water |
| | 2.5% Hexanol |
| | 2.5% Heptanol |
| Secondary Solution: | 2% Lumiphos-530 (contains 35 mM fluorocein isothiocynate) |
| | 1% Polyethylene Glycol-4000 |
| | 5% Dextran-40 |
| | 1% Sorbitan monooleate with 20 moles ethylene oxide (Tween 80) |

The microcapsules were prepared by first loading 20 ml of the secondary solution into the lower chamber of the device at a rate of 3.57 ml/min. The air bubbles were removed by inverting the device and tapping it until they exit the inlet port and are isolated from the chamber. Then 20 ml of the primary solution is added to the upper chamber at rate of 3.57 ml/min. The interface is moved away from the porous barrier into the chamber containing the primary solution by closing all valves and moving both plungers upward at a rate equivalent to that which would move a plunger to fill the chamber at 0.45 ml/min. The microcapsules were allowed to form and toughen or cure for a period of one hour. The microcapsules were then harvested by opening the valve connected to the storage chamber and moving upper plunger downward at 0.9 ml/min. A suitable storage solution for this preparation is the secondary solution that lacks Lumiphos-530. This procedure provides microcapsules of up to 160 microns with a wide size distribution.

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, rather than microprocessor controlled operation of the plungers and valves, manual operation may be used. The membrane may be movable within the chamber, so that separation from the interface is achieved by moving the filter rather than the interface. In addition, microcapsule coatings may rely upon covalent bonds for microcapsule stabilization. All such modifications are intended to be included within the scope of the appended claims.

REFERENCES CITED

The following references to the extent that they provide procedural details supplementary to those set forth herein, are specifically incorporated herein by reference.

Allen, T. M. Interactions of Drug Carriers with the Mononuclear Phagocytic System, in G. Gregoriadis (Ed.) *Liposomes as Drug Carriers*, John Wiley & Sons Ltd., New York, pp. 37–50, 1988.

Allen, T. M., Mehra, T., Hansen, C. and Chin, Y.C., Stealth Liposomes: An Improved Sustained Release System for 1-b-D-Arabinofuranosylcytosine, Cancer Res. 52:2431–39, 1992.

Gabizon, A., et al., Liposome-Associated Doxorubicin: Preclinical Pharmacology and Exploratory Clinical Phase, in G. Lopez-Berestein and I. J. Fidler (Eds.) *Therapy of Infectious Diseases and Cancer*, Alan R. Liss, Inc., New York, pp. 189–203, 1992.

Kimler, B. F, et al., Combination of Aziridinylbenzoquinone and Cis-platinum with Radiation Therapy in the 9 L Rat Brain Tumor Model, Int. J. Radiation Oncology Biol. Phys, 26: 445–450, 1993.

Talsma, H. and Crommelin, D. J. A., Liposomes as Drug Delivery Systems, Part 1: Preparation. Pharmaceutical Technology, pp. 96–106, October 1992.

Todd, P., Separation Physics, in Progress in Astronautics & Aeronautics: Low Gravity Fluid Dynamics and Transport Phenomena, Vol. 130, *American Institute of Aeronautics and Astronautics*, Washington, D.C. (Koster, J. N. and Sani, R. L., Eds., 1990) pp. 539–672.

What is claimed is:

1. A method for preparing a microcapsule comprising the steps of: formulating a primary solution; formulating a secondary solution; adding said primary solution to a first chamber; adding said secondary solution to a second chamber that is adjacent to said first chamber and separated from said first chamber by a porous barrier such that said secondary solution forms an interface with said primary solution at said porous barrier; and allowing said primary and secondary solutions to become quiescent; and moving said interface away from said porous barrier; and allowing microcapsules to form; and isolating said microcapsules by filtration through a porous barrier.

2. The method of claim 1 wherein said step for formulating a primary solution further comprises the steps of preparing a mixture comprising a polymer and at least 75% by volume of an organic solvent.

3. The method of claim 1 wherein said step for formulating a primary solution further comprises the steps of preparing a mixture comprising an organic solvent, a polymer and an oil.

4. The method of claim 2 wherein said step for formulating a primary solution further comprises the steps of preparing a mixture comprising an organic solvent to a final concentration of approximately 75% to 90% by volume and a polymer to a final concentration of approximately 1% to 5% by volume.

5. The method of claim 3 wherein said step for formulating a primary solution further comprises the steps of preparing a mixture comprising an organic solvent to a final concentration of approximately 75% to 90% by volume and a polymer to a final concentration of approximately 1% to 5% by volume and an oil to a concentration of about 1% to 10% by volume.

6. The method of claim 1 wherein said step for formulating a primary solution further comprises the steps of preparing a mixture comprising isopropyl alcohol and glycerol monostearate.

7. The method of claim 1 wherein said step for formulating a primary solution further comprises the step of preparing a mixture comprising a polymer that is insoluble in said secondary solution; and wherein said step for formulating a secondary solution further comprises the step of preparing a mixture comprising a polymer that is insoluble in said polymer of said primary solution and is approximately insoluble in said primary solution.

8. The method of claim 1 wherein said step for formulating a primary solution further comprises the step of preparing a mixture comprising a polymer having an HLB value below 8 and has a hydrocarbon chain length of at least twelve (12) carbon atoms and wherein said step for formulating a secondary solution further comprises the step of preparing a mixture comprising a polymer of 400 to 100,000 Daltons and a surfactant having an HLB that is greater than 12.

9. The method of claim 1 wherein said step for formulating a primary solution further comprises the step of preparing a mixture comprising glycerol monostearate wherein said step for formulating a secondary solution further comprises the step of preparing a mixture comprising polyethylene glycol 1000 and ethoxylated sorbitan monooleate (20).

10. The method of claim 1 wherein said step for formulating a primary solution further comprises the step of preparing a mixture comprising a polymer having an HLB value below 8 and wherein said step for formulating a secondary solution further comprises the step of preparing a mixture comprising a polymer having an HLB value above 12 and a surfactant having an HLB value between 8 and 12.

11. The method of claim 1 wherein said step for formulating a primary solution further comprises the step of preparing a mixture comprising sorbitan monolaurate and wherein said step for formulating a secondary solution further comprises the step of preparing a mixture comprising ethoxylated (10) lanolin and ethoxylated glycerol trioleate.

12. The method of claim 1 wherein said step for formulating a primary solution further comprises the step of preparing a mixture comprising a polymer having an HLB value between 5 and 10 and a surfactant having an HLB value below 5 and wherein said step for formulating a secondary solution further comprises the step of preparing a mixture comprising a polymer having an HLB value above 10.

13. The method of claim 1 wherein said step for formulating a primary solution further comprises the step of preparing a mixture comprising a glycerol monoricinoleate monolaurate and a surfactant having an HLB value below 5 and wherein said step for formulating a secondary solution further comprises the step of preparing a mixture comprising polyethylene glycol 400.

14. The method of claim 1 wherein said step for formulating a primary solution further comprises the step of preparing a mixture comprising a polymer having an HLB value below 8 and wherein said step for formulating a secondary solution further comprises the step of preparing a mixture comprising a polymer of having an HLB value above 12 and a surfactant having an HLB value between the polymer of the primary solution and the polymer of the secondary solution.

15. The method of claim 1 wherein said step for formulating a primary solution further comprises the step of preparing a mixture comprising glycerol monooleate and wherein said step for formulating a secondary solution further comprises the step of preparing a mixture comprising polyvinyl pyrrolidone and ethoxylated (4) sorbitan monostearate.

16. The method of claim 1 wherein said step for formulating a primary solution further comprises the step of preparing an aqueous mixture comprising a polymer having an HLB value between 8 and 11 and wherein said step for formulating a secondary solution further comprises the step of preparing an aqueous mixture comprising a polymer having an HLB between 10 and 12 and a surfactant having an HLB value above 12.

17. The method of claim 1 wherein said step for formulating a primary solution further comprises the step of preparing an aqueous mixture comprising polyethylene glycol 400 distearate and wherein said step for formulating a secondary solution further comprises the step of preparing an aqueous mixture comprising polyethylene glycol monostearate and ethoxylated (20) oleyl ether.

18. The method of claim 1 wherein said step for formulating a primary solution further comprises the step of preparing an aqueous mixture comprising a polymer having an HLB value between 8 and 10 and wherein said step for formulating a secondary solution further comprises the step of preparing an aqueous mixture comprising a polymer having an HLB value greater than 10 and a surfactant having an HLB value of less than 6.

19. The method of claim 1 wherein said step for formulating a primary solution further comprises the step of preparing an aqueous mixture comprising polyethylene glycol 400 distearate and wherein said step for formulating a secondary solution further comprises the step of preparing an aqueous mixture comprising lanolin and diethylene glycerol monooleate.

20. The method of claim 1 wherein said step for formulating a primary solution further comprises the step of preparing a mixture comprising a polymer that dissolves in physiological body fluids.

21. The method of claim 1 further comprising carrying out within a single chamber said step of allowing said capsules to form; and said step of isolating said microcapsules by filtration through a porous barrier; and the additional step of washing said microcapsules by introducing a wash solution into said first chamber containing said microcapsules.

22. The method of claim 1 further comprising the steps of formulating a coating solution, adding said coating solution to microcapsules; and applying electric field to said coating solution and generating a coating around a microcapsule to produce coated microcapsules.

23. The method of claim 22 further comprising the steps of formulating a coating solution by dissolving a cationic composition in said solution, adding said coating solution to said coated microcapsules, applying an electric field to said coating solution and generating a coating around said coated microcapsule.

24. The method of claim 22 further comprising the steps of formulating a coating solution by dissolving type I collagen in said solution, adding said coating solution to said coated microcapsules, applying an electric field to said coating solution and generating a coating around said coated microcapsule.

25. The method of claim 22 further comprising the steps of formulating a coating solution, by dissolving an anionic composition in said solution, adding said coating solution to said coated microcapsules, applying an electric field to said coating solution and generating a coating around said coated microcapsule.

26. The method of claim 22 further comprising the steps of formulating a coating solution, by dissolving a zwitterionic composition in said solution, adding said coating solution to said coated microcapsules, applying an electric field to said coating solution and generating a coating around said coated microcapsule.

27. The method of claim 22 further comprising the steps of formulating a coating solution, by dissolving polyvinyl pyrrolidone in said solution, adding said coating solution to said coated microcapsules, applying an electric field to said coating solution and generating a coating around said coated microcapsule.

28. The method of claim 22 further comprising the steps of formulating a coating solution, by dissolving polyvinyl acetate in said solution, adding said coating solution to said coated microcapsules, applying an electric field to said coating solution and generating a coating around said coated microcapsule.

29. The method of claim 22 further comprising the steps of formulating a coating solution, by dissolving vancomycin in said coating solution, adding said coating solution to said coated microcapsules, applying an electric field to said coating solution and generating a coating around said coated microcapsule.

30. The method of claim 22 further comprising the steps of formulating a coating solution, by dissolving stearylamine in said coating solution, adding said coating solution to said coated microcapsules, applying an electric field to said coating solution and generating a coating around said coated microcapsule.

31. The method of claim 1 wherein the step of moving said interface away from said permeable barrier further comprises moving said interface into said first chamber.

32. The method of claim 22 wherein said electric field is in the range of from approximately 1 to 500 volts/cm.

33. The method of claim 1 further comprising the step of supplying an amount of fluid shear to said interface of less than 100 dynes/cm$^2$ by flowing said primary solution into said first chamber.

34. The method of claim 1 further comprising the step of supplying a small amount of shear by flowing said secondary solution along the fluid interface.

35. The method of claim 1 further comprising the step of formulating an electrophoresis solution, adding said electrophoresis solution to microcapsules, applying an electric field sufficient to cause electrophoretic migration of said microcapsules, and collecting the microcapsules.

36. The method of claim 1 wherein said step for adding a second solution to a second chamber further comprises adding a secondary solution that is hydrophilic relative to said primary solution.

37. A method for preparing a microcapsule comprising the steps of: formulating a primary solution; formulating a secondary solution adding said secondary solution to a first chamber; adding said primary solution to a second chamber that is adjacent to said first chamber and separated from said first chamber by a porous barrier, said primary solution being added to said second chamber so as to create an interface with said secondary solution at said porous barrier; allowing said primary and secondary solutions to become quiescent; moving said interface away from said porous barrier and into said second chamber; allowing microcapsules to form; isolating said microcapsules by filtration through a porous barrier; washing said microcapsules by introducing a solution into the chamber containing said microcapsules; introducing a coating solution into said first chamber; and applying an electric field in the range of approximately 1 to 500 volts/cm into said first chamber.

38. The method of claim 30 further comprising the steps of introducing a coating solution into said first chamber; and applying an electric field into said chamber containing said microcapsules to produce a coating on said coated microcapsules; and isolating said coated microcapsules.

39. A microcapsule produced by a method comprising the steps of: adding a first solution to a first chamber; and adding a second solution that is immiscible with said first solution to a second chamber that is adjacent to said first chamber and separated from said first chamber by a porous barrier, said second solution being added to said second chamber so as to create an interface with said first solution at said porous barrier; allowing said first and second solutions to become quiescent and moving said interface away from said porous barrier; and allowing microcapsules to form; and isolating said microcapsules by filtration through a porous barrier.

40. The microcapsule of claim 32 wherein said method further comprises carrying out within a single chamber said step of allowing said capsules to form; said step of isolating said microcapsules by filtration through a porous barrier; and a step of washing said microcapsules by introducing a wash solution into said first chamber containing said microcapsules.

41. The microcapsule of claim 39 wherein said method further comprises the steps of introducing a coating solution into said first chamber; and applying an electric field in said first chamber to produce coated microcapsules.

42. The microcapsule of claim 39 wherein said step of moving said interface away from said permeable barrier further comprises moving said interface into said first chamber.

43. The microcapsule of claim 39 wherein said step of applying an electric field in said first chamber to produce coated microcapsules further comprises applying an electric field in the range of from approximately 1 to approximately 500 volts/cm.

44. The microcapsule of claim 39 wherein said step of forming microcapsules further includes supplying an amount of fluid shear to said interface of less than 100 dynes/cm$^2$ by flowing said secondary solution into said first chamber.

45. The microcapsule of claim 39 wherein said method further comprises the step of supplying a small amount of shear to said interface by flowing said primary solution along said fluid interface.

46. The microcapsule of claim 39 wherein said method further includes separating said microcapsules into groups by electrophoresis and harvesting said groups into a harvesting chamber.

47. The microcapsule of claim 39 wherein said step for adding a second solution to a second chamber that is adjacent to said first chamber and separated from said first chamber by a porous barrier further comprises adding a second solution to a second chamber that is adjacent to said first chamber and separated from said first chamber by a porous barrier that is hydrophobic if said secondary solution is hydrophobic relative to said primary solution or hydrophilic if said secondary solution is hydrophilic relative to said primary solution.

48. A microcapsule prepared by formulating a primary solution; formulating a secondary solution that is hydrophilic relative to said primary solution; adding said secondary solution to a first chamber; and adding said primary solution to a second chamber that is adjacent to said first chamber and separated from said first chamber by a porous barrier that is hydrophobic if said secondary solution is hydrophobic relative to said primary solution or hydrophilic if said secondary solution is hydrophilic relative to said primary solution, said primary solution being added to said second chamber so as to create an interface with said secondary solution at said porous barrier; allowing said primary and secondary solutions to become quiescent; moving said interface away from said porous barrier and into said first chamber; allowing microcapsules to form; isolating said microcapsules by filtration through a porous barrier; formulating a wash solution; washing said microcapsules by introducing said wash solution into the chamber containing said microcapsules; formulating a coating solution; adding said coating solution to said microcapsules; and generating coated microcapsules.

49. The microcapsule of claim 48 wherein said process further includes applying an electric field to said coating solution after said coating solution is added to said microcapsules.

50. The method of claim 1 further comprising the step of formulating an electrophoresis solution, adding said electrophoresis solution to said microcapsules, applying an electric field to said electrophoresis solution, and collecting groups of microcapsules from the electrophoresis solution.

51. A microcapsule prepared by formulating a primary solution by preparing a mixture containing 1 mg/ml Reglan, 1% polyethylene glycol-400, 5% dextran-40, 1% Tween 80, 0.5% polyvinyl pyrrolidone, 0.05% Cy-3 fluorescent dye; formulating a secondary solution by preparing a mixture containing 5% glycerol monostearate, 92% isopropyl alcohol, 3% iodinated poppy seed oil, 2% water, 1.5% hexanol, 1.5% heptanol adding said secondary solution to a first chamber; and adding said primary solution to a second chamber that is adjacent to said first chamber and separated from said first chamber by a porous barrier, said primary solution being added to said second chamber so as to create an interface with said secondary solution at said porous barrier; allowing said primary and secondary solutions to become quiescent; moving said interface away from said porous barrier and into said first chamber; allowing microcapsules to form; applying an electric field of 14 volts/cm to the microcapsule formation chamber for 1 minute and then reversing the polarity of the electrodes and applying an electric field of 14 volts/cm for a period of 30 seconds; isolating said microcapsules by filtration through a porous barrier; washing the coated microcapsules with water.

52. A microcapsule having a diameter of over 160 microns prepared by formulating a primary solution by preparing a mixture containing 2.5% myverol 1804, 2.5% vitamin E succinate, 88% isopropanol, 5% iodinated poppy seed oil, 2% water, 2.5% hexanol and 2.5% heptanol; formulating a secondary solution by preparing a mixture containing 2% of a solution containing fluorocein isothiocyanate, 1% polyethylene glycol 4000, 5% dextran-40, 1% ethoxylated (20) sorbitan monooleate; adding said secondary solution to a first chamber; adding said primary solution to a second chamber that is adjacent to said first chamber and separated from said first chamber by a porous barrier, said primary solution being added to said second chamber so as to create an interface with said secondary solution at said porous barrier; allowing said primary and said secondary solutions to become quiescent; and moving said interface away from said porous barrier and into said second chamber; and allowing microcapsules to form for one hour.

* * * * *